United States Patent
Gostjeva et al.

(10) Patent No.: US 8,940,500 B2
(45) Date of Patent: Jan. 27, 2015

(54) METHODS FOR IDENTIFYING STEM CELLS BY DETECTING FLUORESCENCE OF CELLS AND SYNCYTIA

(75) Inventors: Elena V. Gostjeva, Winchester, MA (US); William G. Thilly, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 650 days.

(21) Appl. No.: 12/586,372

(22) Filed: Sep. 21, 2009

(65) Prior Publication Data

US 2010/0075366 A1    Mar. 25, 2010

Related U.S. Application Data

(60) Provisional application No. 61/194,076, filed on Sep. 24, 2008.

(51) Int. Cl.
*G01N 33/48* (2006.01)
*G01N 33/50* (2006.01)

(52) U.S. Cl.
CPC ........ *G01N 33/5005* (2013.01); *G01N 33/5026* (2013.01); *G01N 33/5073* (2013.01)
USPC .......................................... 435/40.5; 435/325

(58) Field of Classification Search
None
See application file for complete search history.

(56) References Cited

U.S. PATENT DOCUMENTS

| | | | |
|---|---|---|---|
| 5,369,002 A | 11/1994 | Fukuda | |
| 6,007,996 A * | 12/1999 | McNamara et al. | 435/6.14 |
| 7,427,502 B2 | 9/2008 | Thilly | |
| 7,977,092 B2 | 7/2011 | Gostjeva et al. | |
| 8,465,943 B2 | 6/2013 | Gostjeva et al. | |
| 2009/0081720 A1 | 3/2009 | Gostjeva et al. | |
| 2009/0098562 A1 | 4/2009 | Gostjeva et al. | |
| 2010/0075366 A1 | 3/2010 | Gostjeva et al. | |
| 2013/0203048 A1 | 8/2013 | Gostjeva et al. | |
| 2014/0154672 A1 | 6/2014 | Gostjeva et al. | |

FOREIGN PATENT DOCUMENTS

| | | |
|---|---|---|
| IL | 179972 | 12/2011 |
| JP | 5130042 | 11/2012 |
| KR | 10-1209833 | 12/2012 |
| WO | WO 2005/0097147 A1 | 10/2005 |
| WO | WO 2006/009860 | 1/2006 |
| WO | WO 2008/115517 | 9/2008 |
| WO | WO 2010/036322 A1 | 4/2010 |
| WO | WO 2012/061073 A1 | 5/2012 |

OTHER PUBLICATIONS

Office Action, Japan Application No. 2007-516787, dated Aug. 22, 2011.
Final Office Action, U.S. Appl. No. 12/283,727, dated Sep. 8, 2011.
Office Action, Chinese Application 200580027499.4, dated Oct. 21, 2010.
Office Action, Japanese Application No. 2007-516787, mailed Dec. 14, 2010.
Office Action (Restriction Requirement), U.S. Appl. No. 12/284,521, dated Feb. 17, 2011.
Office Action (Restriction Requirement), U.S. Appl. No. 12/283,727, dated Jan. 27, 2011.
Reply to Restriction Requirement, U.S. Appl. No. 12/283,727, filed Mar. 1, 2011.
Reply to Restriction Rquirement, U.S. Appl. No. 12/284,521, filed Mar. 21, 2011.
Notification of Transmittal of the International Search Report (ISR) and the Written Opinion (WO) of the International Searching Authority, or the Declaration, PCT/US2009/005241 with ISR and WO, mailed Jan. 2, 2010.
Office Action, U.S. Appl. No. 12/283,727, dated Apr. 7, 2011.
Cutts, S.M., et al. "Defective Chromosome Segregation, Microtubule Bundling and Nuclear Bridging in Inner Centromere Protein Gene (Incenp)—Distrupted Mice", *Human Molecular Genetics* 8(7):1145-1155 (1999).
Klijanienko, J., et al., "Fine-Needle Aspiration of Leiomyosarcoma: A Correlative Cytohistopathological Study of 96 Tumors in 68 Patients", *Diagn. Cytopathol.* 28:119-125 (2003).
Özkinay, C. and Mitelman, F., "A Simple Trypsin-Giemsa Technique Producing Simultaneous G- and C-Banding in Human Chromosomes", *Hereditas* 90:1-4 (1979).
Notification Concerning Transmittal of International Preliminary Report on Patentability (IPRP) with IPRP, PCT/US2009/005241, mailed Apr. 7, 2011.
Notice of Allowance, U.S. Appl. No. 12/284,521, dated May 9, 2011.
Kussick, S.J., et al., "A distinctive nuclear morphology in acute myeloid leukemia is strongly associated with loss of HLA-DR expression and FLT3 internal tandem duplication," *Leukemia*, 18: 1591-1598 (2004).
Chen, W., et al., High frequency of NPM1 gene mutations in acute myeloid leukemia with prominent nuclear invaginations ("cuplike" nuclei), *Blood*, 108(5): 1783-1784 (Sep. 1, 2006).
Communication pursuant to Rules 161(1) and 162 EPC, PCT/US2009/005241, mailing date May 30, 2011.
Reply, U.S. Appl. No. 12/283,727, filed Aug. 5, 2011.
Office Action, EP 05761437.2, dated Mar. 26, 2010.
Reply filed, Israeli Appl. No. 179972, Mar. 3, 2010.
Office Action, Israel 179972, dated Jul. 6, 2010.

(Continued)

*Primary Examiner* — Satyendra Singh
(74) *Attorney, Agent, or Firm* — Hamilton, Brook, Smith & Reynolds, P.C.

(57) ABSTRACT

Methods are disclosed for the characterization of the stage of development or pathology of a tissue sample, and for identifying pluripotent metakaryotic stem cells, comprising detecting fluorescence of cells and syncytia in fixed samples treated with a non-fluorescent Schiff's base reagent in the absence of extraneous or exogenously added fluorescent dyes.

9 Claims, 22 Drawing Sheets
(22 of 22 Drawing Sheet(s) Filed in Color)

(56) References Cited

OTHER PUBLICATIONS

Boman, B.M., et al., "Cancer Stem Cells: A Step Toward the Cure," J. Clinical Oncology 26(17):2795-2799 (2008).
Drezek, R., et al., "Light Scattering from Cervical Cells Throughout Neoplastic Progression: Influence of Nuclear Morphology, DNA Content, and Chromatin Texture," J. Biomed. Optics 8:7-16 (2003).
Fujiu, K. and O. Numata, "Reorganization of Microtubules in the Amitotically Dividing Macromolecules of Tetrahymena," Cell Motility and Cytoskeleton 46:17-27 (2000).
Gostjeva, E.V. and W.G. Thilly, "Stem Cell Stages and the Origins of Colon Cancer," Stem Cell Reviews 1:243-252 (2005).
Gostjev, E.V., et al., "Nuclear Morphotypes in Human Embryogenesis and Carcinogenesis: Bell-Shaped Nuclei Show Stem-Like Properties in Vivo," Environmental and Molecular Mutagenesis 47(6): 405 (Jul. 2006).
Gostjeva, E.V., et al. "Bell-Shaped Nuclei Dividing by Symmetrical and Asymmetrical Nuclear Fission Have Qualities of Stem Cells in Human Colonic Embryogenesis and Carcinogenesis," Cancer Gen. and Cytogenetics 164:16-24(2006).
Herrero-Jimenez, P., et al., "Mutation, Cell Kinetics, and Subpopulations at Risk for Colon Cancer in the United States," Mutat. Res. 400:553-578 (1998).
Herrero-Jimenez, P., et al., "Population Risk and Physiological Rate Parameters for Colon Cancer. The Union of an Explicit Model for Carcinogenesis with the Public Health Records of the United States," Mutat. Res. 447:73-116 (2000).
Hirokawa, Mitsuyoshi, et al., "Gastrointestinal Stromal Tumor with Skeinoid Fibers of the Ileum," Diagnostic Cytopathology 23(4), pp. 266-268 (2000).
Itoi, T., et al., "Detection of Telemerase Activity in Biopsy Specimens for Diagnosis of Biliary Tract Cancers," Gastrointestinal Endoscopy 52:380-386 (2000).
Liu, Katharine, et al., "Logistic Regression Analysis of High Grade Spindle Cell Neoplasms," ACTA Cytologica, 43(4), pp. 593-600 (1999).
Lodding, P., et al., "Cellular Schwannoma," Virchows Archiv., 416:237-248 (1990).
Maly, B., et al. "Fine Needle Aspiration Biopsy of Intraparotid Schwannoma: A case report," ACTA Cytologica, 47(6), pp. 1131-1134 (2003).
Merok J.R., et al., "Cosegregation of Chromosomes Containing Immortal DNA Strands in Cells that Cycle with Asymmetric Stem Cell Kinetics," Cancer Res. 62:6791-5 (2002).
Muzio, Lo L., et al., "Primary Introral Leiomyosarcoma of the Tongue: An Immunohistochemical Study and Review of the Literature," Oral Oncology, Elsevier Science, Oxford, GB, 36(6), pp. 519-524, (2000).
Ruddy, J.M.B., and S.K. Majumdar, "Antitumorigenic Evaluation of Thalidomide Alone and in Combination with Cisplatin in DBA2/J Mice," Jour. Biomedicine and Biotechnology, 2:7-13 (2002).
Sakaki, M., et al., "Gallbladder Adenocarcinoma with Florid Neuroendocrine Cell Nests and Extensive Paneth Cell Metaplasia," Endocrine Pathology 11(4):365-369 (2000).
Scheidl, S.J., et al., "mRNA Expression Profiling of Laser Microbeam Microdissected Cells from Slender Embryonic Structures," Am. Jour. Path., 160:801-813 (2002).
Silverman, J.S. and S. Brustein, "Myxoid Dermatofibrohistiocytoma: An Indolent Post-Traumatic Tumor Composed of CD34+ Epitheliod and Dendtritic Cells and Factor Xllla+ Dendrophages," J. Cutan. Pathol. 23:551-557 (1996).
Ying, Z., et al., "Expression of Neural Stem Cell Surface Marker CD133 in Balloon Cells of Human Focal Cortical Dysplasia," Epilepsia, 46(11): 1716-1723 (2005).
Invitation to Pay Additional Fees with Partial International Search Report, PCT/US2005/021504, mailed Mar. 24, 2006.
Notification of Transmittal of International Search Report (ISR) and Written Opinion (WO), with ISR and WO, mailed May 5, 2006, PCT/US2005/021504.
Notification Concerning Transmittal of International Preliminary Report on Patentability (IPER), with IPER and Written Opinion, PCT/US2005/021504, mailed Jan. 4, 2007.
Notification of Transmittal of the International Search Report (ISR) and the Written Opinion (WO) of the International Searching Authority, or the Declaration, PCT/US2008/003604 with ISR and WO, mailed Jan. 19, 2009.
Invitation to Pay Additional Fees and, Where applicable, Protest Fee with Partial International Search Report, PCT/US2008/003604, mailed Aug. 12, 2008.
Notification Concerning Transmittal of International Preliminary Report on Patentability (IPRP) with IPRP, PCT/US2008/003604, mailed Oct. 1, 2009.
Office Action, Israeli Appl. No. 179972 with reply due Feb. 7, 2010.
Clark, A.D., et al., "Isolation and therapeutic potential of human haemopoietic stem cells," Cytotechnology, 41(2-3): 111-31 (Mar. 2003) (Abstract only).
Communication pursuant to Article 94(3) EPC, European Application No. 05761437.2, dated Feb. 28, 2012.
Munoz, L., et al., Acute myeloid leukemia with MLL rearrangements: clinicobiological features, prognostic impact and value of flow cytometry in the detection of residual leukemic cells, Leukemia, 17: 76-82 (2003).
Office Action, Korean Application No. 10-2007-7001187, dated Mar. 21, 2012.
Office Action, Canadian Application No. 2,570,422, dated Feb. 23, 2012.
Response to Communication pursuant to Article 94(3) EPC, European Application No. 05761437.2, filed Oct. 5, 2010.
Office Action, Chinese appl. 200580002749934, dated Mar. 27, 2012.
Abe, T., et al., "Myocyte Differentiation Generates Nuclear Invaginations Traversed by Myofibrils Associating with Sarcomeric Protein mRNAs," Journal of Cell Science, 117: 6523-6534 (Sep. 2004).
Communication pursuant to Rules 161(1) and 162 EPC, EP 09736317.0, dated May 30, 2011.
Office Action, Japanese Appl. No. 2007-516787, mailed Jun. 4, 2012.
Transmittal of International Preliminary Report on Patentability (IPRP), "Wound Healing Metakaryotic Stem Cells and Methods of Use Thereof", with IPRP, PCT/U52011/057513, mailed May 10, 2013.
Decision on Rejection, Chinese appl. 200580027499.4, dated Apr. 28, 2013.
Amendment After Final, U.S. Appl. No. 12/283,727, filed Mar. 4, 2013.
Notice of Allowance, U.S. Appl. No. 12/283,727, dated Mar. 8, 2013.
Canada 2,570,422, Reply filed Aug. 22, 2012.
Reply, EP 05761437.2 filed Sep. 4, 2012.
Notification of Transmittal of International Search Report (ISR) and Written Opinion (WO), PCT/US2011/0057513 with ISR and WO, mailed Feb. 28, 2012.
Third Office Action, Chinese appl. 200580027499.4, dated Sep. 19, 2012.
RCE & Amendment, U.S. Appl. No. 12/283,727, filed Oct. 5, 2012.
Final Office Action., U.S. Appl. No. 12/283,727, dated Nov. 2, 2012.
Notification of Transmittal of International Search Report (ISR) and Written Opinion (WO), PCT/US2012/040361 with ISR and WO, mailed Oct. 1, 2012.
Gostjeva, E.V., et al., "Metakaryotic stem cell lineages in organogenesis of humans and other metazoans," Organogenesis 5(4):191-200 (2009).
Gruhl, A.N., et al. "Human fetal/tumor metakaryotic stem cells: pangenomic homologous pairing and telomeric end-joining of chromatids," Cancer Genetics and Cytogenetics 203(2):203-208 (2010).
Refinetti, P., "Analysis of familial risk for prostate, colon and femalbreast cancer in Sweden," Master's project in Bioengineering and Biotechnology, pp. 1-109:Retrieved from the Internet Jul. 26, 2012: infoscience.eptl.ch/record/173435/files/Master_thesis_Final.pdf.
Thilly, W.G., "Metakaryotic Biology, a Revolution in Cancer Stem Cell Research," Retrieved from the internet Jul. 26, 2012, www.med.uio.no/klinmet/english/research/news-and-events/events/guest-lectures-seminars/2012/william-thilly.html.

(56) References Cited

OTHER PUBLICATIONS

Goodlad, R. A., et al., "Morphometry and Cell Proliferation in Endoscopic Biopsies: Evaluation of a Technique," *Gastroenterology*, 101: 1235-1241 (1991).
Kanzaki, M., el al., "Bilateral Endobronchial Metastasis in Postoperataive Stage I Pulmonary Adenocarcinoma," *Diagn. Ther. Endosc.*, 6(3):141-145 (2000).
Rittershaus, A. C., and Appelman, H. D., "Benign Gastrointestinal Mesenchymal BUMPS: A Brief Review of Some Spindle Cell Polyps With Published Names," *Arch. Pathol. Lab. Med.*, 135: 1311-1319 (2011).
Thilly, W. G., et al., "Metakaryotic stem cell nuclei use pangenomic dsRNA/DNA intermediates in genome replication and segregation," *Organogenesis*, 10(1): 1-9 (2014).
Wong, W.-M., et al., "Histogenesis of human colorectal adenomas and hyperplastic polyps: the role of cell proliferation and crypt fission," *Gut*, 50: 212-217 (2002).
Office Action from Canadian Application No. 2,570,422, "Methods for Identifying Stem Cells Based on Nuclear Morphotypes," mailed Mar. 7, 2013.
Office Action from European Application No. 09 736 317.0, "Methods for Identifying Stem Cells by Detecting Fluorescence of Cells and Syncytia," mailed Aug. 28, 2013.
Reply from Canadian Application No. 2,570,422, "Methods for Identifying Stem Cells Based on Nuclear Morphotypes," filed Sep. 9, 2013.
Reexamination Decision from Chinese Application No. 200580027499.4, "Methods for Identifying Stem Cells Based on Nuclear Morphotypes," mailed Nov. 4, 2013.
Office Action from Chinese Application No. 200980146118.2, "Methods for Identifying Stem Cells by Detecting Fluorescence of Cells and Syncytia," mailed Nov. 22, 2013.
International Preliminary Report on Patentability from International Application No. PCT/US2012/040361, "dsRNA/DNA Hybrid Genome Replication Intermediate of Metakaryotic Stem Cells," mailed Dec. 12, 2013.
Reply from European Application No. 09 736 317.0, "Methods for Identifying Stem Cells by Detecting Fluorescence of Cells and Syncytia," filed Dec. 20, 2013.
Office Action from Chinese Application No. 200580027499.4, "Methods for Identifying Stem Cells Based on Nuclear Morphotypes," mailed Dec. 23, 2013.
Office Action from Indian Application No. 2561/CHENP/2011, "Methods for Identifying Stem Cells by Detecting Fluorescence of Cells and Syncytia," mailed Dec. 26, 2013.
Restriction Requirement from U.S. Appl. No. 13/879,675, mailed Jan. 28, 2014.
Office Action from Japanese Application No. 2011-527826, "Methods for Identifying Stem Cells by Detecting Fluorescence of Cells and Syncytia," mailed Feb. 17, 2014.
Office Action from European Application No. 05 761 437.2, "Methods for Identifying Stem Cells Based on Nuclear Morphotypes," mailed Feb. 26, 2014.
Restriction Requirement from U.S. Appl. No. 13/914,152, mailed Mar. 11, 2014.
Office Action from Chinese Application No. 200980146118.2, "Methods for Identifying Stem Cells by Detecting Fluorescence of Cells and Syncytia," mailed Apr. 23, 2014.
Office Action from Canadian Application No. 2,570,422, "Methods for Identifying Stem Cells Based on Nuclear Morphotypes," mailed May 7, 2014.
Office Action from European Application No. 09 736 317.0, "Methods for Identifying Stem Cells by Detecting Fluorescence of Cells and Syncytia," mailed May 7, 2014.
Office Action from U.S. Appl. No. 13/879,675, mailed May 14, 2014.
Reply from European Application No. 09 736 317.0, "Methods for Identifying Stem Cells by Detecting Fluorescence of Cells and Syncytia," filed Jun. 3, 2014.
Office Action from European Application No. 09 736 317.0, "Methods for Identifying Stem Cells by Detecting Fluorescence of Cells and Syncytia," mailed Jun. 24, 2014.
Notice of Allowance from Chinese Application No. 200580027499.4, "Methods for Identifying Stem Cells Based on Nuclear Morphotypes," mailed Jul. 4, 2014.
Reply from European Application No. 12727007.2, "dsRNA/DNA Hybrid Genome Replication Intermediate of Metakaryotic Stem Cells," mailed Jul. 28, 2014.
Reply from European Application No. 09 736 317.0, "Methods for Identifying Stem Cells by Detecting Fluorescence of Cells and Syncytia," filed Aug. 18, 2014.
Office Action from Chinese Application No. 201180062704.6, "Wound Healing Metakaryotic Stem Cells and Methods of Use Thereof," mailed Aug. 27, 2014.
Office action from U.S. Appl. No. 13/914,152, mailed Sep. 19, 2014.
Office Action from Chinese Application No. 200980146118.2, "Methods for Identifying Stem Cells by Detecting Fluorescence of Cells and Syncytia," mailed Jun. 15, 2013.

* cited by examiner

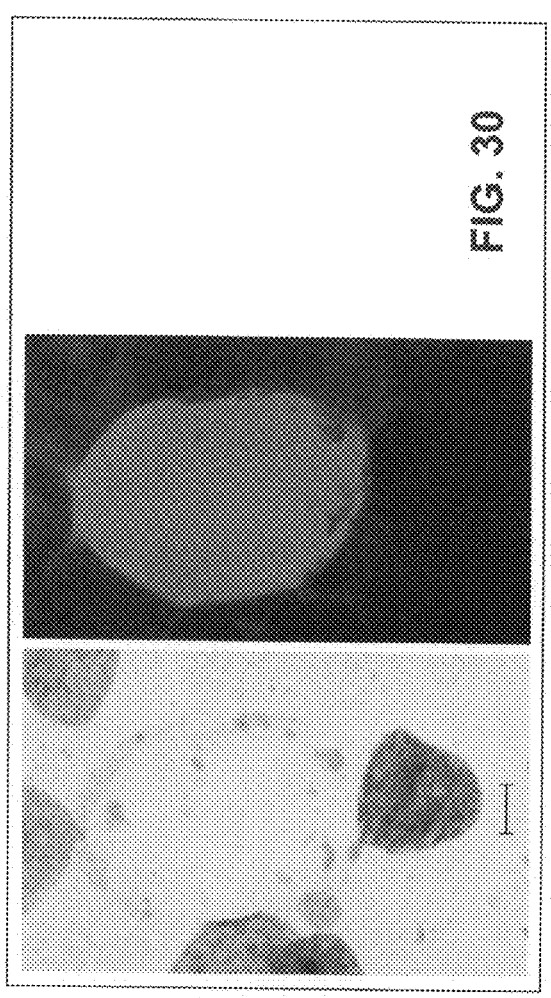

METHODS FOR IDENTIFYING STEM CELLS BY DETECTING FLUORESCENCE OF CELLS AND SYNCYTIA

RELATED APPLICATION

This application claims the benefit of U.S. Provisional Application No. 61/194,076, filed on Sep. 24, 2008.

The entire teachings of the above application(s) are incorporated herein by reference.

BACKGROUND OF THE INVENTION

The processes that lead to growth and differentiation in animal embryos, fetuses, neonates and juveniles share certain characteristics with the processes that lead to growth and differentiation of cell types preceding and creating tumors. Methods that recognize antigenic molecules in tumors and fetuses have shown that there are many molecules observable in both fetuses and tumors that are not observed in adult organs. In the nineteenth century it was argued that tumors might arise from residual embryonic or fetal cells in adults. Current views point to the existence of self-renewing stem cells in which genetic changes occur in lineal descent from embryonic to adult stem cells that create tumor stem cells that give rise to tumors. The summarized argument is that a single normal fetal juvenile tissue stem cell could be the progenitor of pre-neoplastic stem cells, one of which in turn gives rise to a founding stem cell for tumors, which in turn give rise to a founding stem cells for clonal metastases and transplanted tumors. Based on the clear presence of histologically differentiable cell types in pre-neoplastic lesions, tumors and metastases, and by analogy to embryological growth and development, it can be inferred that the originating stem cell of tissues, pre-neoplastic lesions, tumors and metastases must be capable of differentiation as well as self renewing growth. If the stem cell theory of tumor growth is correct, then there is a clear and present need to identify, sort, classify and manipulate tumor stem cells. However, identification or isolation of such cells has not been described in the art.

SUMMARY OF THE INVENTION

The present invention derives from the process of identification of and methods for classifying organ-specific and/or tumor stem cells and other stem cell forms in a mammal, including a human, cell culture, and tissue samples including pre-neoplastic lesion or tumor samples. The invention relates to methods for identifying stem cells and syncytia containing stem cell nuclei by determining or detecting the presence or absence of, or determining or measuring the intensity of, the fluorescence of the stem cells, or syncytia containing one or more stem cell nuclei. More particularly, the fluorescence is present in balloon-like organelles of a stem cell. These balloon-like organelles are also referred to herein as cytoplasmic structures or cytoplasmic compositions. As used herein cytoplasmic structures or cytoplasmic compositions include the cytosol portion of the cytoplasm, cellular membranes, cellular organelles and combinations thereof. In a syncytium of interest that comprises at least one stem cell nucleus (and frequently comprises two or more stem cell nuclei), the syncytium comprises a fluorescent cytoplasm (or cytosol) surrounding or engulfing one or more stem cell nuclei (e.g., in the inter-nuclear spaces of the syncytium) in the cytoplasm of the syncytium of interest. As further described herein, the "stem cell nuclei" particularly refers to "bell-shaped nuclei". Stem cells containing bell-shaped nuclei are also referred to herein as metakaryotes.

As used herein, a fluorescent stem cell or syncytium is a stem cell or syncytium that is fluorescent in the absence of extraneous or exogenously added fluorescent dyes. The fluorescence identifying metakaryotic stem cells and or syncytia is created by reaction with exogenous non-fluorescent chemical that creates a fluorescent product by reaction with materials present in the stem cells and/or syncytia. More particularly, the non-fluorescent chemical comprises a Schiff's base. The intense fluorescence is present in the cytoplasm of the stem cell. Fluorescence is specifically absent from the bell shaped metakaryotic stem cell nuclei.

In one embodiment, the fluorescent stem cell or syncytium is detected after fixation using such suitable reagents as acid-alcohol mixtures and subsequent treatment with a non-fluorescent reagent that reacts with components of the stem cell or syncytium to create a fluorescent product. Suitable acid-alcohol mixtures for stem cell fixation include acetic acid-ethanol; Carnoy's fixative; 3:1 methanol-glacial acetic acid; 6:3:1 ethanol-chloroform-acetic acid; 3:1 ethanol-acetic acid; and the like. Suitable non-fluorescent reagents include a Schiff's base reagent, Feulgen reagent, fuchsin and the like. As used herein, a non-fluorescent reagent is not, by itself, fluorescent (examples of reagents that are, by themselves, fluorescent include FITC, green fluorescent protein, Texas Red, and the like).

In another embodiment, the fluorescent stem cell or syncytium is detected after staining with a non-fluorescent reagent (e.g., a Schiff's base reagent, Feulgen reagent, fuchsin, and the like).

Thus, one method of the present invention is based on identifying a metakaryotic stem cell of interest, or multinuclear syncytium of interest, wherein the syncytium of interest comprises one or more stem cell nuclei (e.g., frequently the syncytium of interest comprises two or more stem cell nuclei), wherein the stem cell nucleus is characterized by a bell-shaped nucleus, by detecting or visualizing fluorescent balloon-like organelles (cytoplasmic structures or cytoplasmic compositions, but not nucleoplasm) in the stem cell or syncytium comprising one or more stem cell nuclei.

It should be noted that the metakaryote stem cells described herein are distinct from goblet cells that also have an enlarged, balloon-like cytoplasm that can be rendered fluorescent after fixation and staining with suitable Schiff's base reagents such as fuchsin. Goblet cells as described in the literature of histology and medical texts are found in many tissues including the lungs and colon associated with the production of mucins found in large quantities in the goblet cell cytoplasm. As in single metakaryotic stem cells, the nuclei of goblet cells are also eccentrically located at one end of their balloon shaped cytoplasm. However in a metakaryotic stem cell, the distinct bell shaped nucleus is in close physical proximity with the balloon shaped cytoplasm which is partially engulfed by the mouth of the bell. In contrast, the nucleus of a goblet cell is spheroid or ovoid and usually separated from the cytoplasm by a narrow neck or stem as in a wine glass or "goblet". It is important to emphasize this key difference: goblet cells do not have a bell-shaped nucleus and are a distinct cell type from metakaryote stem cells which do have a bell-shaped nucleus.

In one embodiment, a metakaryote stem cell that fluoresces in the absence of extraneous or exogenously added fluorescent dyes or reagents as described herein is an organ-specific stem cell and is found in many, but not all, human fetal organs during development including organs of the digestive, respiratory, nervous and musculo-skeleton systems, a cancer stem cell, a fetal juvenile stem cell or an adult stem cell. Specifically, metakaryote stem cells with bell shaped nuclei of the veins and arteries of the developing human vascular system have not been found to contain material within their cytoplasm that fluoresces in the absence of extraneous or exogenously added fluorescent dyes or reagents as described herein. Thus, in one embodiment, a metakaryote stem cell that fluoresces in the absence of extraneous or exogenously added fluorescent dyes or reagents as described herein is not a vascular stem cell.

As described above, the stem cells and syncytium of interest are fluorescent without extraneous fluorescent material/dye added to samples in order to visualize the stem cells and syncytium of interest. Thus, the discovery of the unique characteristic of stem cell/syncytial fluorescence without extraneous fluorescent material/dye will greatly facilitate the identification of stem cells/syncytia in tissue samples such as tumor tissue biopsy samples. Such samples can be quickly scanned by manual, automatic or semi-automatic fluorescent scanning techniques for surgical pathology and surgical oncology diagnoses.

As described in U.S. Pat. No. 7,427,502 "Methods for Identifying Stem Cells Based on Nuclear Morphotypes", the teachings of which are incorporated herein in their entirety, nuclear morphotypes, the modes of nuclear division and the involvement of nuclei of particular morphotypes in multicellular aggregates and multinuclear syncytia among all cells in a cell culture, tissue, pre-neoplastic lesion or tumor sample are indicative of stem cells. Identification of organ-specific or tumor stem cells can be made on the basis of a particular nuclear morphotype alone. Multiple forms (nuclear morphotypes) of clear and reproducible non-spherical nuclei in fetal tissue, pre-neoplastic lesions (adenomas of the colon) and neoplastic lesions or tumors (adenocarcinomas of the colon, carcinomas of the pancreas) were observed, but were absent in normal adult tissue such as colonic crypts or liver parenchyma. These morphotypes, disclosed in U.S. Pat. No. 7,427, 502, include nuclei of size and shapes previously unreported in the annals of histology or pathology of human tissues. One remarkable nuclear morphotype has the form of cups or bells with an open "mouth"-designated "bell-shaped". These bell-shaped nuclei were observed in symmetric nuclear divisions resembling the separation of two stacked paper cups.

These "cup-from-cup" divisions are also remarkable in that they are amitotic, e.g., do not involve condensation of all human chromosomes and separation as in mitosis. They are symmetrical nuclear divisions insofar as two apparently identical bell-shaped nuclei result from the cup-from-cup division. These bell-shaped nuclei are also observed to undergo amitotic asymmetric nuclear divisions in which a bell-shaped nucleus appeared to give rise to an enclosed nucleus of one of the other nuclear morphotypes. This production of the original bell-shaped nucleus and a nucleus of a different morphotype is the first visualization of an asymmetrical nuclear division. The appearance of a heteromorphic nuclear morphotype distinct from the bell-shaped nucleus in asymmetrical amitotic cell divisions involving bell-shaped nuclei is disclosed herein to distinctly define a cell with a heteromorphic nuclear morphotype distinct from the phenotype of a cell with a bell-shaped nucleus. Asymmetric nuclear division is widely considered a necessary characteristic of stem cells in normal development. The discovery of nuclear morphotypes common to both fetal tissue, pre-neoplasia and neoplasia bear on the hypothesis that tumors are a re-expression of fetal phenotypes, specifically stem cells forming clonal populations with derived differentiated cellular phenotypes.

Now, as described herein, in addition to nuclear morphotype, an additional characteristic unique to stem cells has been discovered. Fluorescence of stem cells and syncytia containing stem cell nuclei in the absence of extraneous or exogenously added fluorescent dyes provide a rapid means of identifying and enumerating stem cells/syncytia in cell and tissue samples.

In one embodiment of the present invention, detection of the fluorescent stem cell/syncytium in the absence of extraneous or exogenously added fluorescent dyes is indicative of normal, pre-neoplastic, neoplastic or metastatic tissue, depending on the tissue source of the sample. In another embodiment, the presence of fluorescent stem cells/syncytia in the absence of extraneous or exogenously added fluorescent dyes is indicative of pre-neoplasia or neoplasia. In a particular embodiment, the tissue/tumor sample suitable for the methods described herein is obtained by surgical excision.

Typically the sample is physically or chemically fixed, e.g., with a fixing agent comprising methanol and acetic acid, Carnoy's fixative before further treatment with a non-fluorescent reagent such as the Schiff's base in Feulgen stain as described herein. Fixation should be performed in fewer than thirty minutes after surgical fixation after which time cellular degradation of bell-shaped nuclei is observed. Typically the cells of the tissue/tumor sample are partially dissociated by tissue maceration and spreading. In a particular embodiment of the present invention, the stem cells/syncytia are detected using fluorescence microscopy. (The short-hand notation "stem cell/syncytium or syncytia" will be used herein to describe not only stem cells but syncytium comprising stem cell nuclei, and in particular cells and syncytium containing bell-shaped nuclei.)

In another embodiment, the invention is directed to a method for characterizing the stage of development or pathology of a tissue sample, comprising detecting the fluorescent stem cell/syncytia in the absence of extraneous or exogenously added fluorescent dyes. In one embodiment, the stage of development is selected from the group consisting of: embryonic, fetal, neonatal, juvenile and adult stages of development. Additionally, the detection of the fluorescent stem cells/syncytia can lead to the identification of macromolecular markers that are indicative of a particular stage of development or pathology, such as pre-neoplasia or neoplasia. Such markers can be an antigen, cell-surface marker, nucleic acid, protein, phosphorylated protein, glycosaminoglycans or metabolites. In another embodiment, the fluorescent balloon-like structures associated with bell-shaped nuclei can be found to be the site of protein synthesis and or post-translational processing, e.g., a cytoplasmic structure.

Further embodiments of the present invention include methods of identifying agents which inhibit stem cell proliferation. The steps of such methods include treating a cultured tissue or cell sample comprising stem cells, or syncytia comprising stem cell nuclei, with a candidate agent; determining the presence of and/or intensity of, or number of, fluorescent stem cells in the absence of extraneous or exogenously added, fluorescent dyes, or fluorescent syncytia containing stem cell nuclei in the absence of extraneous or exogenously added fluorescent dyes, in the tumor or cell sample in culture and comparing the presence of and/or intensity of fluorescence of the cells or syncytia in a culture treated with the candidate agent with the presence of and/or intensity of, or number of, fluorescent stem cells or syncytia containing stem cell nuclei, in a culture not treated with the candidate agent, wherein a decrease in the number of, or intensity of, fluorescent stem cells, or syncytia containing stem cell nuclei, or a cessation of increase of same (e.g., wherein the number of cells do not decrease but do not increase either, that is they remain at essentially a static number) is indicative of an effective agent which kills or inhibits the proliferation of stem cells.

Another embodiment includes methods of identifying an anti-tumorigenic agent comprising treating a cultured tumor tissue or cell sample with a candidate agent determining the presence of and/or intensity of, or number of, of fluorescent stem cells in the absence of extraneous or exogenously added fluorescent dyes, or fluorescent syncytia containing stem cell nuclei in the absence of extraneous or exogenously added fluorescent dyes, in the tumor or cell sample in culture; and comparing the presence of and/or intensity of fluorescence of the cells or syncytia in a culture treated with the candidate anti-tumorigenic agent with the presence of and/or intensity of fluorescence of cells or syncytia in a culture not treated with the candidate anti-tumorigenic agent, wherein a decrease in the number of, or intensity of, fluorescent stem cells, or syncytia containing stem cell nuclei, is indicative of an effective anti-tumorigenic agent.

A further embodiment of the present invention includes methods of identifying an agent which inhibits the proliferation of stem cells, comprising treating a test mammal with a candidate agent; determining the presence of and/or intensity or number of fluorescent stem cells in the absence of extraneous or exogenously added fluorescent dyes, or fluorescent syncytia containing stem cell nuclei in the absence of extraneous or exogenously added fluorescent dyes, contained within a sample obtained from the mammal; and comparing the presence of and/or intensity or number of fluorescence of the cells or syncytia obtained from the mammal treated with the candidate agent with the presence of and/or intensity of fluorescence of cells or syncytia obtained from a mammal not treated with the candidate agent, wherein a failure to increase the number of, or intensity of, fluorescing stem cells, or syncytia containing stem cell nuclei, is indicative of an effective agent which inhibits the proliferation of stem cells.

Also encompassed are methods of identifying an anti-tumorigenic agent comprising treating a mammal having a tumor with a candidate agent, determining the presence of and/or intensity of fluorescent stem cells in the absence of extraneous or exogenously added fluorescent dyes, or fluorescent syncytia containing stem cell nuclei in the absence of extraneous or exogenously added fluorescent dyes, contained within a tumor sample obtained from the mammal; and comparing the presence of and/or intensity or number of fluorescence of the cells or syncytia obtained from the mammal treated with the candidate anti-tumorigenic agent with the presence of and/or intensity of fluorescence of cells or syncytia obtained from a mammal having a tumor but not treated with the candidate anti-tumorigenic agent wherein a decrease in the number of, or intensity of, fluorescing stem cells, or syncytia containing stem cell nuclei, is indicative of an effective anti-tumorigenic agent.

The value of the methods described herein to specifically identify these previously unrecognized cells as stem cells by their fluorescence in the absence of extraneous or exogenously added fluorescent dyes, nuclear morphotype, modes of nuclear division and/or involvement in multi-nuclear structures in normal and tumor tissues is clear. The processes make it possible to specifically recognize stem cells and other fetal and tumor-specific nuclear morphotypes, permit their isolation and study, and provide for their use in tests to discover which of many plausible preventative or therapeutic regimens for cancer are effective. The methods described herein also provide means to discover specific stem cells for regeneration and transplantation therapies for human tissues and organs (e.g., tissue restoration therapy).

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows fetal gut, 5-7 weeks, at low magnification (140×) with stained nuclei (left image) and phase contrast/fluorescent images of different gut sections (right image). Distinctly non-spherical nuclei are arranged in a linear order (indicated by dashed lines) that is defined by "tube-like" structures in phase contrast images. These tube-like structures appear throughout the gut sections observed with other cell groupings interspersed among the tubes. FIG. 2B shows a phase contrast image (left frame) and stained nuclei image (middle) of the identical gut section overlaid (right) to demonstrate that the apparent linear orientation of the nuclei are in fact constrained by the tube-like structure or syncytium, which is itself about 50 microns in diameter. Magnification (280×) of the nuclei (middle frame) shows that these non spherical nuclei appear to be in the form of cups or bells. FIG. 2C shows magnified images (1400×) of nuclei in linear array. These arrayed nuclei have a reproducible bell-shape that is apparently hollow. The "head-to-toe" orientation of the bells is preserved in all embryonic tubes observed, but tubes snake backwards and forwards such that parallel tubes can have locally anti parallel bell-shaped nuclei orientation. Scale bars, 100 µm at low and 5 µm at high magnification.

FIG. 3A: Symmetrical amitosis: a bell-shaped nucleus apparently emerges from a bell-shaped nucleus. A variety of bell-shaped morphotypes are observed but their amitoses show indistinguishable bell-shaped morphotypic characteristics such as the ratio bell mouth width/length as shown in these three examples; FIG. 3B: Asymmetrical amitosis: a solid nuclear form apparently emerges from within the bell-shaped nucleus. Shown are four images in which a spherical condensed nucleus is seen to be formed deep in the bell, and apparently emerges with nucleoplasmic connections to the bell before separating completely; FIG. 3C: spherical uncondensed nucleus coming out of the mouth of the bell-shaped nucleus; FIG. 3D: egg-shaped ("oval") nucleus emerging from bell; FIG. 3E: bean-shaped ("kidney-shaped") nucleus emerging from bell; FIG. 3F: cigar-shaped nucleus emerging from bell. Scale bar, 5 µm.

FIG. 4A shows crypts of about 2000 spherical and ovoid nuclei occasionally (<1/100) contained a recognizable bell-shaped nucleus (arrow in lower left corner) located at the bottom of the crypt (right corner: enlarged image of the nucleus). FIG. 4B shows the crypt base with another bell-shaped nucleus among other nuclear morphotypes peculiar to the base. FIG. 4C shows various morphotypes of interphase and mitotic nuclei of the walls and luminal surface in a well spread crypt. The enlarged images show: (i) spherical and ovoid interphase nuclei, (ii, ii) early prophases of spherical and oval shaped nuclei, and (iv) an anatelophase nucleus. Scale bars, 100 µm for low and 5 µm for high magnification images.

FIG. 5A shows a large branching crypt characteristic of adenomas. Crypt bases and luminal openings are regularly arranged in a manner similar to normal colonic sections. FIG. 5B shows an irregular crypt like structure that was also observed throughout the adenoma samples. Typically two, but sometimes one, four or even eight bell-shaped nuclei (insert) appear at the base of these large (>4000 cell) irregular crypts. FIG. 5C shows a cluster of cells of similar nuclear morphotype containing one bell-shaped nucleus. These simple clusters contain 16, 32, 64, and 128 total cells. Left panel: Feulgen Giemsa stain. Right panel: phase contrast fluorescent image. FIG. 5D illustrates different contexts in which bell-shaped nuclei appear in adenomas: (i) cluster with 31 ovoid nuclei and one bell-shaped nucleus, (ii) multiple bell-shaped nuclei in "shoulder-to-shoulder" arrangement, (iii) bell-shaped nuclei arranged in "shoulder-to-shoulder" pattern (arrowed) in larger "circles", (iii) irregular mixture of ~250 nuclei of with several bell-shaped nuclei suggestive of nascent crypt bases found scattered throughout adenomas. FIG. 5E shows an irregular crypt like structure containing apparently clonal patches of cells of five different nuclear morphotypes with one bell-shaped nucleus (arrow) at the base. Scale bar, 100 µm for low and 5 µm for high magnification images.

FIG. 6A shows very large crypt like structures (>8000 cells), with branches with frequent break points. The bases of these structures were indistinguishable from those of normal colonic crypts except for the presence of two (typically) bell-shaped nuclei as in adenomas. The base to lumen orientation of crypt like structures preserved in adenomas is not observed in adenocarcinomas in which crypt orientations appear to be random. The arrow indicates a small ~250 cell crypt-like structure commonly found near the surface of the tumor. FIG. 6B shows shoulder to shoulder groupings of bell-shaped nuclei found throughout the tumor interior. FIG. 6C shows the interior tumor mass with multiple examples of bell-shaped nuclei locally oriented in both shoulder-to-shoulder and head-to-toe configurations. The head-to-toe orientation is found only in the tumor interior, the shoulder-to-shoulder orientation found both interiorly and near the tumor surface among the crypt like structures. Bell-shaped nuclei account for ~0.2% of all nuclei in the tumor interior. Scale, 100 µm for low and 5 µm for high magnification images.

FIG. 7A shows symmetrical amitoses creating two bell-shaped nuclei of distinct morphologies in irregular crypts. The arrow in the left image indicates the bottom of the bell of the newly arising nucleus. FIG. 7B shows asymmetrical amitosis creating a spherical nucleus. FIG. 7C shows asymmetrical amitoses creating oval shaped nucleus. FIG. 7D shows symmetrical amitoses forming "cigar" shaped nuclei. FIG. 7E shows asymmetrical amitosis creating a "sausage" shaped nucleus with curious dark staining element (upper arrow) distinct from what appear to be condensed chromosomes at the lip of the bell-shaped nucleus (lower arrow). Scale, 5 µm.

FIGS. 29 and 30 are high resolution photographs of the HT29 cultured and stained as described herein. The photographs on the left show the cells with standard transmittance microscopy and illustrate the purple staining of nuclei (note the bell-shaped nuclei). The photographs on the rights are the same cells observed using fluorescence microscopy. As can be seen, intense fluorescence (green) of balloon-like structures are intimately associated with but separate from a bell-shaped nucleus of metakaryote HT29 cells.

DETAILED DESCRIPTION OF THE INVENTION

Figure 1:
FIG. 1 shows nuclear morphotypes observed in interphase and early prophase (E. P.) cells in human embryo gut, normal colonic mucosa, adenomas and adenocarcinomas. *Bell-shaped nuclei are rarely observed in the epithelial crypts of adult colon. Scale bar, 5 µm.

The present invention relates to the unexpected discovery that metakaryotic stem cells and syncytia containing distinct bell-shaped stem cell nuclei are rendered intensely fluorescent in fixed surgical specimens and cell cultures by treatment with reagents such as the Schiff's base fuchsin present in the commonly used Feulgen reagent. Since said fluorescence is created in the absence of extraneous or exogenously added fluorescent dyes it does not suffer from the difficulties of background fluorescence in automatic scanning as for tumor stem cells in a surgical sample. These stem cells and syncytia are present throughout fetal gut at (5-7 wks), colonic adenomas, and adenocarcinomas, and are rarely found in normal (non-neoplastic) epithelial crypts of the adult colon. These "heteromorphic nuclear morphotypes" (e.g., nuclear morphotypes that differ from the normally spheroid or ovoid nuclei of cells in adult organs), were observed in fetal tissues and less commonly in adult tissues. One remarkable nuclear morphotype has a nucleus shaped like a hollow bell (approximately 10-15 microns in height and approximately 7-12 microns in bell mouth diameter). These bell-shaped structures divide symmetrically by an amitotic process resembling the separation of two paper cups.

Notably, as described herein, bell-shaped nuclei that are physically associated with balloon-like cytoplasmic structures are rendered intensely fluorescent when acetic acid: ethanol fixed specimens are treated with the non-fluorescent Schiff's base fuchsin found in Feulgen reagent (in the absence of extraneous or exogenously added fluorescent dyes). Further, syncytia containing stem cell nuclei (e.g., bell-shaped nuclei) are also fluorescent after the identical process of fixation and treatment with Feulgen reagent. These balloon-like cytoplasmic structures and syncytia were found to fluoresce upon excitation with light provided through a halogen lamp. Fluorescence is the property of some atoms and molecules to absorb light at a particular wavelength and to subsequently emit light of longer wavelength. The observation that the balloon-like cytoplasmic structures and syncytia comprising bell-shaped nuclei fluoresce (in the absence of extraneous or exogenously added fluorescent dyes), allows for the rapid identification of cells with bell-shaped nuclei. Thus, the fluorescent properties of these stem cells/syncytia allow for their detection in methods useful in characterizing tissues samples (e.g., neoplastic, pre-neoplastic) or the developmental stage of tissue samples (e.g., fetal).

As described herein, a fluorescent stem cell or syncytium is a stem cell or syncytium that is fluorescent in the absence of extraneous or exogenously added fluorescent dyes. Fluorescent syncytia containing a stem cell can be detected by a certain degree of autofluorescence after fixation alone (e.g., using Carnoy's fixative; 3:1 methanol-glacial acetic acid; 6:3:1 ethanol-chloroform-acetic acid; 3:1 ethanol-acetic acid; and the like).] Fluorescent stem cells and syncytia can be detected by intense fluorescence after fixation (e.g., using Carnoy's fixative; 3:1 methanol-glacial acetic acid; 6:3:1 ethanol-chloroform-acetic acid; 3:1 ethanol-acetic acid; and the like) and further staining with a non-fluorescent reagent (e.g., a Schiff reagent, Feulgen stain, fuchsin, and the like). Thus, in one embodiment, tubular syncytia containing bell-shaped nuclei in human organs of approximately the 4th through 13th week of gestation and of human tumors when fixed with Carnoy's reagent display a modest fluorescence in the absence of extraneous or exogenously added fluorescent dyes. In a further embodiment, tubular syncytia containing bell-shaped nuclei in human organs of approximately the 4th through 13th week of gestation and of human tumors fixed with Carnoy's and further stained with Feulgen reagent produces tubular syncytia with bell-shaped nuclei that display an intense fluorescence. In another embodiment, large balloon-shaped cytoplasmic entities to which bell-shaped nuclei are attached are not fluorescent upon simple Carnoy fixation, but instead the balloon-shaped cytoplasms are extraordinarily fluorescent upon reaction with Feulgen stain. Said intensely fluorescent balloon-shaped cytoplasms have been observed in human organs developing from the fifth week, and in the 12th-14th week comprise nearly all entities with bell-shaped nuclei. This is true also for human preneoplastic lesions such as colonic polyps and a wide assortment of human tumors.

Where bell-shaped nuclei are indicative of a particular developmental stage, e.g., fetal tissue, the identification of balloon-like structures and/or syncytia associated with bell-shaped nuclei, e.g., by detecting their fluorescence in the absence of extraneous or exogenously added fluorescent dyes, can also be indicative of a particular developmental stage. Alternatively, biopsies of lesions suspected on the basis of anatomical position and mass to have tumorigenic potential detection of balloon-like structures/syncytia associated with bell-shaped nuclei is indicative of neoplasia or pre-neoplasia.

In addition, as cells with bell-shaped nuclei have been observed to divide asymmetrically, to give rise to several other forms of nuclear morphotypes in the same fetal organ, pre-neoplastic or neoplastic lesion, they are pluripotent. As pluripotency is a hallmark feature of stem cells, the detection of balloon-like structures associated with bell-shaped nuclei allows for a rapid screening of cells for the identification and isolation of stem cells. Methods for detecting and isolating cells with such balloon-like structures, e.g., methods for sorting and isolation based on the fluorescence of cells with these balloon-like structures, are known in the art. Cells isolated in such a way from non-neoplastic tissues have enormous potential in, for example, regenerative tissue therapies and wound healing.

In addition to the bell-shaped nuclei described above, at least seven other nuclear forms were observed to emerge from bell-shaped nuclei in asymmetrical amitoses. Cells containing these derivative nuclear forms subsequently divide by mitoses forming clonal populations of identical nuclear morphotypes in embryos, adenomas and adenocarcinomas. Cells with bell-shaped nuclei thus are responsible for both net growth and differentiation in embryonic gut, adenomas and adenocarcinomas and fulfill the requirements for generative, multipotent stem cells in fetal organogenesis and carcinogenesis. The specific differential occurrence of bell-shaped nuclei in cells demonstrating both symmetrical and asymmetrical amitoses theoretically required for net stem cell growth and differentiation in fetal/juvenile tissue sample as opposed to adult tissue, allows for one skilled in the art of microscopic histology/pathology to classify cells as stem cells or not stem cells according to their nuclear morphology.

A concept shared in both embryology and oncology is that the multiple cell types that are observed in organs and tumors derived from particular organs arose from precursor "stem" cells capable of net growth by symmetrical cell divisions in which a cell division produces two identical precursor "stem" cells and differentiation by asymmetrical cell division producing one precursor "stem" cell and one differentiated cell. This differentiated cell may then divide an additional number of times to create a large number of differentiated cells that eventually reach a non-dividing terminal stage followed by programmed cell death. An "extinction" division occurs when a cell differentiates into two more highly differentiated cells.

The term "stem cell" has many different levels of definition in the scientific literature. In general it is meant to comprise the set of cells that maintain an undifferentiated or partially differentiated phenotype but can in certain circumstances give rise to cells with different phenotypes. The use of the generic term and more specific terms used herein distinguish among types of stem cells based on the scientific observations that comprise the teachings disclosed herein.

The term "embryonic stem cell" as used herein comprises the set of cells in the early mammalian embryo that divide by ordinary mitosis and can, upon transplantation into a uterine environment, give rise to a complete placenta and fetus. They are thus characterized as "totipotent". Such cells can be cultivated ex vivo, dividing by mitosis, to form very large numbers of embryonic stem cells—each capable of giving rise to a placenta and fetus. It is not known whether or not any embryonic stem cells persist as such in a growing mammalian fetus, neonatal, juvenile or adult animal. It is possible that certain clusters of undifferentiated cells found throughout tissues in adult mammals represent colonies of totipotent embryonic stem cells. With regard to nuclear morphotype, this form of stem cell contains spherical or nearly spherical nuclei that are not bell-shaped.

The term "fetal juvenile stem cell" as used herein comprises the set of cells and multinuclear syncytia observed in human fetuses by the fifth week of gestation and in human pre-neoplastic, neoplastic and metastatic lesions that contain bell-shaped nuclei. As used herein, "syncytia" are multinuclear structures lacking cell septa. Multiple nuclei are present but they are not segregated into individual compartments within the syncytia by membranes. The fetal juvenile stem cell undergoes both symmetrical nuclear division creating two identical bell-shaped nuclei, and asymmetrical nuclear division creating one bell-shaped nucleus and one nucleus of the several heteromorphic nuclear morphotypes observed in tissue and tumor samples such as, for example, kidney-shaped, cigar-shaped, sausage-shaped, oval or spherical nuclei that subsequently increase in number by mitosis. Both symmetrical and asymmetrical nuclear divisions of bell-shaped nuclei are amitotic insofar as there is no general condensation of the genome as chromosomes in the bell-shaped nuclei. In the bell-shaped nuclei there is no formation of a mitotic spindle, and no condensation or separation of chromosomes as in prophase, metaphase, anaphase and telophase as observed for more than a century and previously believed to be the only relevant form of nuclear division in mammalian cells (including mammalian tumors) save for the meiotic divisions of oogenesis and spermatogenesis. Symmetrical division permits the net growth of fetal juvenile stem cells and presumably accounts for the growth of tissues and organs throughout fetal, neonatal and juvenile stages of life. Asymmetrical divisions of fetal juvenile stem cells permits creation of cells with alternate phenotypes and presumably accounts for the differentiated cell types that comprise the parenchyma of developing and growing organs. Insofar as nuclear morphotype is a recognizable characteristic of a cell and/or nucleus, cells differing in nuclear morphotype can be characterized as differing in cellular or nuclear phenotype without reference to a characteristic other than nuclear morphotype.

The term "regenerative stem cell" as used herein comprises the theoretical form of cell lies in a dormant state in fetal, juvenile and adult tissues until required to regenerate a portion of tissue or organ that has been destroyed by injury or disease. It is unknown whether the divisions of regenerative stem cells, that would be of necessity expected to be both symmetrical and asymmetrical are mitotic or amitotic in nature.

The term "maintenance stem cell" as used herein comprises the theoretical form of cell that by regular asymmetrical cell division creates a first transitional cell that, by subsequent mitotic division and ultimately programmed cell death, defines the differentiated turnover unit of differentiated cell tissues such as, for example, the colonic crypts. Turnover occurs in fetal and juvenile tissues but the maintenance stem cells of each turnover unit are expected to be bell-shaped and to divide symmetrically to create a new fetal juvenile maintenance stem cell to replace juvenile cells lost by programmed cell death. Asymmetrical division of the adult maintenance stem cell would also create a differentiated transitional cell (non-stem) and a new adult maintenance stem cell. As very few colonic crypts have been observed with the bell-shaped nuclei characteristic of the observed fetal juvenile stem cells in the base of the crypts, it is reasonable to conclude that fetal juvenile stem cell nuclei undergo a metamorphosis marking the cessation of net growth of juvenile organs and the beginning of the adult stage of life. It is unknown whether the asymmetric divisions of adult maintenance stem cells are mitotic or amitotic in nature.

The term "pre-neoplastic stem cell" as used herein describe mononuclear cells comprising the observed bell-shaped nuclei found in the base of adenomatous colonic crypts. These cells are observed in small aggregates of cells of identical nuclear morphotypes, in large clusters of such aggregates in which each aggregate creating the cluster contains nuclei of the same morphotype with different aggregates contain nuclei of differing morphotype, and in sub-regions of the colonic pre-neoplastic lesions. These cells can have nuclei arranged in a "shoulder to shoulder" relationship. Syncytia containing bell-shaped nuclei have not been observed in human colonic pre-neoplastic lesions nor have the individual bell-shaped nuclei been observed in symmetrical nuclear division, a condition interpreted as consistent with the slow growth of pre-neoplastic lesions at approximately the growth rate of the juvenile tissues from which they were derived, i.e. a doubling time of about six to nine years.

The term "neoplastic stem cell" or "tumor stem cell" as used herein comprises the bell-shaped nuclei found in cancerous tumors, e.g., adenocarcinomas of the human colon, metastases of colonic tumors and tumors of the human pancreas, lung, breast and ovary. These neoplastic stem cells are differentiated from pre-neoplastic stem cells by their presence in all of the observed multicellular aggregates of pre-neoplasia, but, in addition, are found in multinuclear tubular syncytia. Neoplastic stem cells are observed to undergo amitotic nuclear divisions in the symmetrical "cup-from cup" process and asymmetrically in which heteromorphic nuclei emerge from bell-shaped nuclei both intra- and extra-syncytially. The syncytia found in tumors are less extensive than those observed in early fetal gut tissue, but the syncytia and bell-shaped structures undergoing symmetrical nuclear divisions appear to be clear distinguishing characteristics between pre-neoplastic and neoplastic tissue.

The heteromorphic nuclear morphotypes described herein can also be found in cells and syncytia derived from, for example, a tissue sample or cells grown in culture. The methods described herein can be applied to any tissue sample to identify cells or syncytia containing the heteromorphic nuclear morphotypes. In particular, tumor tissue samples can be used to identify and enumerate heteromorphic nuclear morphotypes.

As used herein, "tumor" refers to an abnormal growth of tissue resulting from progressive multiplication of cells serving no physiological function that is beneficial to the carrier (also referred to as a "neoplasm"). A "benign" tumor is a tumor limited to the site of origin without invasion of the surrounding tissue. Malignant tumors are those that can or do spread by invasion of surrounding tissue and metastasis while benign tumors neither invade nor metastasize. As used herein, "neoplastic" refers to a cellular condition of rapid net cell growth giving rise to a lethal tumor, whether benign or malignant. Neoplastic cells lead to tumors, although not necessarily invasive or metastatic tumors. "Cancer" refers to the disease of one or more rapidly growing colonies of cells that cause death by interfering with bodily functions. Cancer cells can break away from a primary tumor, penetrate into lymphatic and blood vessels, circulate through the bloodstream, and grow in a new site (metastasize) in normal tissues elsewhere in the body.

As used herein, a "pre-cancerous condition" is characterized as a slowly growing colony that, if unchecked, has the potential to give rise to cancer (e.g., neoplastic tumors). This condition is characterized, for example, by the presence of an abnormal microanatomical structure or structures such as, for example, polyps in the colon or bell-shaped nuclei within an adult tissue sample.

The "net stem cell growth rate" is the rate (divisions per unit time) of symmetrical fetal juvenile stem cell divisions that account for net growth of a tissue, organ or organism. In general stem cell net growth rates decrease with increased development of an organism throughout fetal, neonatal and juvenile life to zero in adults.

Tumors display many of the characteristics of the adult organ/system from which they are derived including formation of complex multi cellular structures, such as, for example, colonic crypts in adenocarcinomas of the colon. Insofar as tumors have been derived from a single precursor cell that had the ability of both net growth and differentiation, it has been reasoned that "tumor stem cells" must exist and share many characteristics organ-specific stem cells (partially undifferentiated cells capable of giving rise to specific organ cells and tissues). For example, in the case of the cells of the bone marrow from which leukemia arises, certain antigens have been recognized that allow identification of marrow cell sub-populations that contain one or a small number cells capable of giving rise to a complete blood cell system on transplantation. Similarly a subfraction of tumor cells can be recognized by specific antigens expressed by some tumor cells. According to this logic, one cell among the sub-population so recognized gives rise to a new differentiated tumor upon experimental transplantation of mixtures of tumor cells. Continuing with this reasoning, the "organ-specific stem cells" and "tumor stem cells" exist among such antigen expressing sub-populations. These antigens are used to identify and isolate cell populations containing at least one pluripotent stem cell, but will also identify a large majority of cells that cannot act as stem cells. None of the cells of these populations as isolated have been found to undergo asymmetrical cellular divisions that are considered a "shibboleth" of true stem cells or organs and tumors.

Presented here are methods for identifying cells that are in fact "organ-specific stem cells" or "tumor stem cells" as opposed to subfractions of organs or tumors enriched for such cells. The identification is based on the fluorescence and heteromorphic nuclear morphotypes and nuclear divisions and/or arrangements described herein. With these methods, it would be possible to isolate such stem cells and discover their specific biochemistry and molecular biologies with the goals of isolating cells permitting organ regeneration, interfering with the growth of pre-cancerous lesions and/or the killing of the cells specifically responsible for tumor growth and reappearance after attempts at therapy. The association of fluorescent balloon-like structures with bell-shaped nuclei can, for example, allow for the identification and isolation of stem cells in the absence of exogenous fluorophores, as the structures themselves will fluoresce after excitation with appropriate wavelengths of light.

Such organ-specific and tumor stem cells are further identified in fetal organs, tumors and tumor metastases by their participation as a class in two specific previously unreported, microscopically visible forms of nuclear division. In the first of these two forms of nuclear division there is no general condensation of chromosomes and formation of a mitotic apparatus; instead one bell-shaped nucleus appears to give rise to an identical bell-shaped nucleus in a manner similar to separation of two paper cups. This symmetrical, amitotic division provides for the net growth of stem cells in fetal and tumor samples. In the second form of stem cell-specific nuclear division there is also no general condensation of chromosomes and formation of a mitotic apparatus; instead one bell-shaped nucleus appears to give rise to a bell-shaped nucleus and a nucleus of a nucleus having one of the several nuclear morphotypes observed in fetal tissue and tumor samplers (FIG. 3). However, heteromorphic nuclei emerging by asymmetric nuclear division condensed chromosomal complements as in mitotic prophase may be observed. This asymmetrical, amitotic division provides for creation of differentiated cells by stem cells in fetal tissue and tumors. Mitotic division of nuclei without bell-shaped nuclei are observed in fetal tissue and tumor samples creating the majority of total cells in such samples. Thus the process of identification of stem cells permits direct observation of cells with bell-shaped nuclei undergoing both symmetrical and asymmetrical nuclear divisions, both necessary for classification as organ-specific and tumor-specific stem cells.

Such organ-specific and tumor stem cells are further identified in fetal organs, tumors and tumor metastases by their participation as a class in specific previously unreported multi nuclear-structures resembling long tubes in which bell-shaped nuclei are regularly aligned in a fashion resembling a series of separated paper cups retaining the head-to-toe relationship as in the stacked cup set.

These stem cell-specific nuclear morphotypes (bell-shaped), specific forms of nuclear division (symmetrical and asymmetrical amitotic nuclear divisions) and specific form of participation in multinuclear structures (long multinuclear tubes) are essentially absent from adult organs. However, the stem cell-specific nuclear morphotype is observed among the cells of pre-neoplastic lesions and rarely, as single nuclei, widely dispersed in adult organs (for example, somewhat fewer than one in two million nuclei of adult colonic crypts have been found to be bell-shaped nuclei).

The unexpected discovery of these heteromorphic nuclear morphotypes and their differential occurrence in stem cells, normal adult tissue and tumor tissue allows for one skilled in the art to classify cells according to their fluorescence or nuclear morphology. In addition, stem cells can be isolated based on their fluorescence or nuclear morphology, anti-tumorigenic agents can be screened or identified based on the appearance or disappearance of tumor-specific morphotypes, and tissue samples can be classified (e.g., normal or abnormal; neoplastic or non-neoplastic) by determining the fluorescence or morphotypes present in the cells of the tissue. As a result of this cell classification, a diagnosis can be made as to whether or not an individual potentially preneoplastic or neoplastic lesion is a cancerous or pre-cancerous lesion. Although particular methods allow for the visualization of these stem cells, any method that allows for the identification and evaluation of fluorescence or nuclear morphotype is suitable for the classification of cells, tissues and samples, and subsequent diagnosis of disease, as well as provide the basis for assays used to identify anti-tumorigenic agents (e.g., agents effective in inhibiting or decreasing tumorigenic cell growth). Such methods include, but are not limited to, phase contrast microscopy, confocal microscopy, two electron or two wavelength microscopy, direct detection of fluorescent structures/syncytia associated with bell-shaped nuclei, and small angle scatter flow cytometry.

For the purposes of the present invention, thick, ~0.5 mm, sections of normal adult human colonic epithelium, colonic adenomas, colonic adenocarcinomas, and fetal gut were prepared for microscopic observation as described in the Examples below. The thickness of the tissue sheet layer should be at least the thickness of an intact cell (and not just a section or slice of the cell). An array of large spheroidal and non-spheroidal nuclear forms appeared in all samples as summarized in FIG. 1. All of the samples contained the spheroid and ovoid nuclei normally observed in histological sections of adult colonic crypts but also contained extraordinary, previously unreported nuclear morphotypes. Embryonic tissue contained nuclei shaped like bells, tapered cigars, kidney beans, sausages and small spheres. Normal adult colonic crypts contained an occasional bell-shaped nucleus in the crypt bases but the vast majority were the large spheres and ovoid structures. In some views it appears that cell nuclei near the crypt bases may be "discoid". In adenomas and adenocarcinomas the nuclear shapes, in addition to the spheroid and ovoid nuclei, included tapered cigars and an additional form that looks like a cigar with a bitten off end dubbed "bullet shaped".

Crypt structures were preserved by the preparative procedure and were clearly observed in normal colon, adenomas and adenocarcinomas. The ~0.5 mm sample sections employed were much thicker than the largest nuclear form observed, the sausage shape, which was ~40 microns in length. All of the nuclear structures, except the 4 micron "condensed spherical nuclei", had at least one internal axis longer than the 5 micron sections usually employed in pathological evaluations. Furthermore, there is a fair degree of morphological variation among nuclei that can be classified as "bell-shaped" or "cigar shaped" etc., suggesting independent lineages and physiological functionalities.

The phenomena of bell-shaped nuclei, their symmetric and asymmetric forms of amitosis, or the collection of nuclear morphotypes in adult, pre-neoplastic, neoplastic and embryonic tissue described herein have not been previously reported. The tubular encasement of linearly arrayed bell-shaped nuclei in embryos and adenocarcinomas is also apparently a novel observation. The reason that they have not been previously observed may lie in the differences between standard histological practices and those employed and disclosed herein. Two clear procedural differences are evident. First, all tissues for fixation were sectioned and fixed within a short period of time (for example, within 30 minutes) of surgical removal. Preparations after 30 minutes may begin to show degradation of the nuclear forms, although careful tissue preparation may prevent degradation. Second is the difference between thin section procedures practiced in medical pathology and thick section fixation protocols, disclosed herein—the latter preserving, and the former apparently destroying, the structures/conditions that maintain these nuclear shapes.

Amitosis, as a phenomenon, has been reported in a number of protozoans and primitive metazoans (Orias, E., 1991, *J. Protozool.*, 38:217-221; Prescott, D., 1994, *Proc. Natl. Acad. Sci. USA*, 92:136-140). However, these amitoses were unlike those reported here insofar as protozoan amitotic nuclear division occurred by formation of a nuclear cleft and pinching off two separate approximately equal nuclei (Fujiu, K. and Numata, O., 2000, *Cell Motil. Cytoskeleton*, 46:17-27). Amitotic divisions of the sort similar to those seen in protozoans have been reported, however, in a number of different tumors (Okuyama, S. 1991, *Tohoku J. Exp. Med.*, 164:247-249; Okuyama, S., 1992, *Tohoku J. Exp. Med.*, 168:445-448; Elias, H. and Fong, B., 1978, *Hum. Pathol.*, 9:679-684; Elias, H. and Hyde, D., 1982, *Hum. Pathol.*, 3:635-639).

The observations showing that the arrangement of chromosomes in early prophase nuclei of the mitotic cells maintains the shape of the interphase nucleus also deserve attention. It appears that the different chromosomes form a highly structured mosaic that may have important consequences in defining a cell's phenotype. The relationship between the spatial arrangement of chromosomes in interphase nuclei and cell physiology is an active area of exploration (Misteli, T., 2001, *Science*, 291:843-847; Thomas, C. et al., 2001, *Proc. Natl. Acad. Sci. USA*, 99:1972-1977; Parada, L. et al., 2004, *Exp. Cell Res.*, 296:64-70).

Based on the observations cited below, cells with bell-shaped nuclei are pluripotent cells that represent the generative cell of the developing and growing tumors and pre-neoplastic lesions such as, for example, colorectal tumors, adenomas and adenocarcinomas. Thus, fluorescence and the bell-shaped nuclear morphotype is indicative of pluripotent stem cells and can be used as diagnostic criteria for pre-neoplastic and neoplastic tissue in adult tissue samples. In addition, the organization of bell-shaped nuclei (e.g., into tube-like structures or spider-web-like structures) can be further indicative of the progression of tumor development (e.g., neoplasia or metastatic tumors).

The pluripotency of bell-shaped nuclei is demonstrated by the images of multiple forms of nuclei emerging from bell-shaped nuclei in asymmetrical amitotic divisions. Insofar as egg-, sausage-, kidney-, bullet- and cigar-shaped nuclei are observed emerging from bell-shaped nuclei and no other nuclear forms are observed, they represent the set of functions necessary for the tissue in which they reside to persist. There can indeed be multiple forms of cells with bell-shaped nuclei as suggested by the morphological variations among bell-shaped nuclei observed.

The numbers and symmetrical amitotic frequencies of cells with bell-shaped nuclei are consistent with the generative element of this hypothesis. They are observed in large numbers in fetuses, rare in normal adult colon free of neoplasia, present, in small numbers (for example, about 1,000) in adenomas of a few cubic millimeters and large numbers (for example, less than about 1,000,000) in adenocarcinomas of several cubic centimeters. Their division rates in the fetus and adenocarcinomas are estimated to be approximately 20-30 divisions per year consistent with the estimated net growth rates of colonic adenocarcinomas (Herrero Jimenez, P. et al., 1998, *Mutat. Res.*, 400:553-578). Their symmetrical amitotic fraction in adenomas is less than 1/1000 and none have been seen to date. This negative observation is important in itself. The frequency of cell divisions for the generative cell or "cell at risk of promotion" in human colonic pre-neoplastic lesions has been estimated by calculation to be about one in six to nine years (Herrero Jimenez, P. et al., 2000, *Mutat. Res.*, 447:73-116; Gostjeva, E. V. and W. G. Thilly, 2005, *Stem Cell Reviews* 2: 243-252). Assuming amitosis could be recognized for a three hour period, a frequency of less than 6/100,000 would be expected. Thus, the very low symmetrical amitotic rate of adenomas is consistent with expectation for the generative cells of colonic pre-neoplasia.

It is possible that the cells with bell-shaped nuclei are phased out at the end of juvenile growth. Retinoblasts phase into retinocytes in early childhood and remove the risk of retinoblastoma in retinoblastoma gene heterozygotes (Knudson, A., 1971, *Proc. Natl. Acad. Sci. USA*, 68:820-823). It could be that colon tumor "initiation" by mutations in genes such as APC prevents this phasing out process. If so, bell-shaped nuclei should be found in the bases of colonic crypts in neonates and juveniles.

From the appearance of bell-shaped nuclei in embryonic and carcinogenic tissues, relationships between embryogenesis and carcinogenesis can be inferred. Cancer researchers have considered tumors to reflect characteristics of embryos for more than a century. Erenpresia, J. and Helmtrud, I. (1999, *Mech. Aging and Develop.*, 108:227-238) cited J. Cohnheim (1875, *Virchows Arch.*, 65:64; 1877-1880, Vorelesungen uber allgemeine Pathologie. Ein Handbuch fur Artzte und Studierende. Berlin, Hirchswald 1 2 691S) as first hypothesizing that tumors arise from embryonic or fetal cells that inappropriately persist in adult tissues. The expression of carcino-embryonic antigens in tumors and appearance in tumors of a wide spectrum of gene products, mRNAs and proteins, that are also found in embryos and/or fetuses has reinforced the broad hypothesis that oncogenesis involves the appearance of cells with embryonic and or fetal qualities. It should be noted that many writers use the terms embryonic and fetal interchangeably including the ambiguous translation of the 19th century German pathologists. (Herein we delineate the embryonic/fetal boundary as the transition from mitotic embryonic stem cells to amitotic fetal stem cells with bell-shaped nuclei) The finding of morphological cell types essentially identical in form, amitotic and mitotic behavior in adenocarcinomas and fetal colon calls for a more specific restatement of the "carcino-embryonic" hypothesis as a "carcino-fetal" hypothesis in terms closely echoing Cohnheim and using the more recent arguments and experimental demonstrations indicating the existence of tumor stem cells (Pardal et al., 2003, *Nature Rev.*, 3:895-902).

These new observations, integrated into the body of cancer research and ideas of the past 130 years, suggest a simple hypothesis about the origin and characteristics of most late onset (adult) colonic adenomas and adenocarcinomas: tumor initiating mutations, e.g., APC gene inactivations, occur in a cell with a bell-shaped nucleus before this cell form is phased out during or at the end of the juvenile period. Such initiated cells with bell-shaped nuclei would simply continue to divide and create new colonic crypts at the same rate as they did in juveniles (Herrero Jimenez, P. et al., 1998, *Mutat. Res.*, 400: 553-578; Herrero Jimenez, P. et al., 2000, *Mutat. Res.*, 447: 73-116). The resultant local crowding creates the "polyp". Either actively, by an additional genetic change or changes (including changes in gene imprinting), or passively by biochemical changes occurring within the growing adenoma, a single cell with a bell-shaped nucleus reverts to an earlier fetal condition and gives rise, as in the fetus, to a rapidly growing array of cells almost indistinguishable from fetal tissue. Untreated, this continued growth leads to colonic obstruction and/or metastases and death.

In the most general sense these observations point to a highly ordered nature of carcinogenesis in which distinctly non-chaotic behavior is observed in adenomas that preserve the slow but constant growth rate of juveniles and in adenocarcinomas that recreate an ordered ensemble of cell types and growth rates observed during fetal organogenesis. In the sense that the existing biological forms have been selected from a myriad of degenerate possibilities ("trying all combinations"), it is perhaps not surprising that carcinogenesis in humans might represent a rare but simple failure to cease juvenile growth and a subsequent rare reversion to an ordered fetal cell state.

These observations suggest that cells with bell-shaped nuclei would be targets for more specific and therefore more effective forms of tumor prevention and therapy. Were it possible to drop the net growth rate of pre-neoplastic colonies by 50%, most late onset cancer types would not appear during a human lifetime of 100 years (Herrero Jimenez, P. et al., 1998, *Mutat. Res.*, 400:553-578; Herrero Jimenez, P. et al., 2000, *Mutat. Res.*, 447:73-116). It is reasonable to believe that cells with heteromorphic nuclear morphotypes such as, for example, bell-shaped nuclei are the tumor stem cells in adenomas and adenocarcinomas of the colon, one might target the mechanisms that confer their special characteristics in DNA synthesis and segregation either in symmetrical divisions of net growth or the asymmetric divisions that provide the cells that divide by mitosis and provide the bulk of the tumor mass. It may be that these cell types or entubated bell-shaped nuclei operate under different biochemical rules and that these, if understood, might also be exploited in tumor prevention and/or therapy (see, for example, the findings of Otto Warburg who discovered marked differences in mitochondrial biochemistry among embryonic/fetal, adult organ and cancer tissues (Warburg, O., 1956, *Science*, 123:309-314; Warburg, O. et al., 1960, *Z. Naturforsch B.*, 15B:378-379).

Reference to basic texts on invertebrates shows that a large sausage shaped nucleus exists among the ciliated protozoans such as the pertirich Vorticella and the heterotrich "Stentor has a remarkable type of large nucleus resembling a string of beads . . . " (Buchsbaum, R. et al., 1971, *Animals Without Backbones,* 3rd ed., University of Chicago Press, Chicago, Ill.). These peculiarities of nuclear metamorphoses might even be linked in evolutionary time with the biochemistry of cells surviving in the pre-oxic environment insofar as they appear to grow in developing organs, adenomas and adenomas in local milieu that would be expected to be oxygen poor prior to neo vascularization. Warburg's discovery indicating that amino acids provide the oxygen reducing equivalents for ATP generation in fetuses and tumors suggests selection of a phenotype that treats oxygen as the limiting nutrient.

The heteromorphic nuclear morphotypes (e.g., bell-shaped nuclei) thus appear to represent a three fold physiological nexus uniting evolutionary biology, organogenesis and oncogenesis. To the genetic cycle of meiosis and mitosis, symmetrical and asymmetrical amitotic stages of lineal descent between the mitotic divisions of the post fertilization period and the mitotic divisions that create most of the cellular mass of an animal must now be added.

The present invention is specifically directed to methods of classifying cell types based on fluorescence, nuclear morphology, their involvement in symmetrical and asymmetrical amitoses and their association in multicellular aggregates. For example, a tissue sample obtained from a mammal can be classified based on the presence or absence of fluorescent balloon-like cytoplasmic structures in the absence of extraneous or exogenously added fluorescent dyes or syncytia comprising heteromorphic nuclear morphotypes (e.g., bell-shaped nuclei, cigar-shaped nuclei and bullet-shaped nuclei). As FIG. 1 demonstrates, heteromorphic nuclear morphotypes are present in different stages of development and also at different stages of tumor development. For example, bell-shaped nuclei are found in fetal samples, rarely in adult samples, and prevalently in adenoma and adenocarcinoma samples. This supports the notion that heteromorphic nuclear morphotypes can be used to identify fetal juvenile stem cells as well as neoplastic stem cells in adult tissues. These results demonstrate a previously undocumented link between fetal stem cells and cancer stem cells. Thus, heteromorphic nuclear morphotypes that are indicative of fetal juvenile stem cells in fetuses are also indicative of cancer stem cells in adult tissues.

Figure 2A:
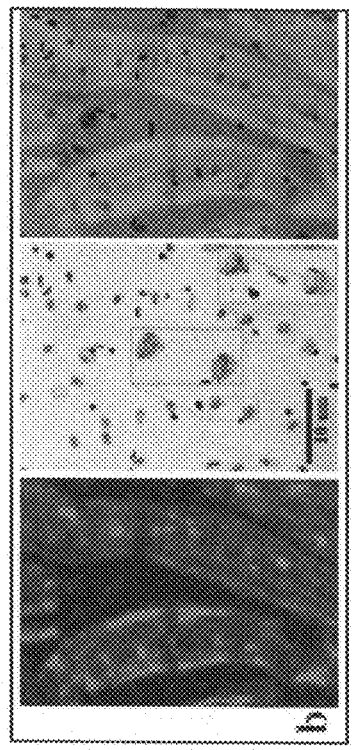
FIGS. 2A-2C show microscopic images of embryonic gut.
Figure 2B:
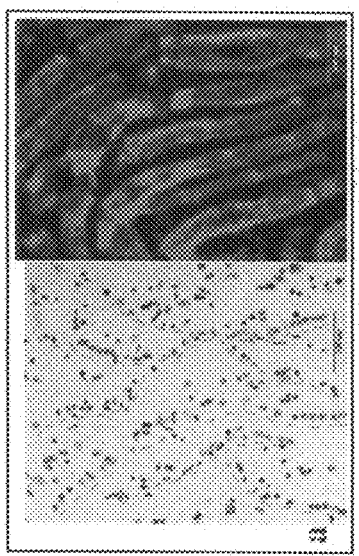
Figure 2C:
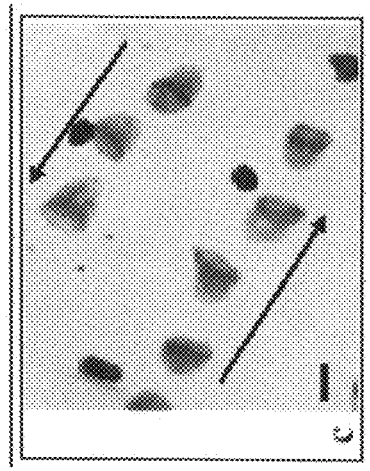

In addition, FIGS. 2A-2C show that heteromorphic nuclear morphotypes align in tube-like structures. As these tube-like structures are present in fetal samples and contain heteromorphic nuclear morphotypes (e.g., bell-shaped nuclei, cigar-shaped nuclei and bullet-shaped nuclei), the tube-like structures themselves can be used as indicia of fetal juvenile stem cells or neoplastic (e.g., tumor or cancer) stem cells in adult tissues.

Alternatively, the arraying of heteromorphic nuclear morphotypes into syncytia as shown in FIG. 5A-5E is indicative of differences between adenomas and adenocarcinomas. Therefore, the arrangement of nuclear morphotypes in multinuclear structures in a tissue sample can be used to differentiate among neoplastic samples at different stages of disease.

As heteromorphic nuclear morphotypes have been observed in other adult tissues and tumor samples (e.g., liver), one of skill in the art would recognize a pre-neoplastic or neoplastic lesions based on the presence of heteromorphic nuclear morphotypes in any adult tissue.

The present invention is also directed to methods for identifying agents that inhibit the proliferation of stem cells/syncytia and anti-tumorigenic agents based on the effect of said agents in reducing the number or slowing the increase in number of metakaryotic stem cells identified by their intense fluorescence after fixation and treated with a suitable non-fluorescent reagent such as fuchsin found in Feulgen reagent. appearance or disappearance of fluorescence, i.e. in the absence of extraneous or exogenously added fluorescent dyes. This mode of identification of metakaryotic stem cells can be independently verified in any surgical sample or cell culture by the simultaneous identification of heteromorphic nuclear morphotypes specifically associated with pre-neoplastic or neoplastic tissues (e.g., bell-shaped nuclei, cigar-shaped nuclei and bullet-shaped nuclei). Agents that inhibit or slow the growth/proliferation of stem cells are also useful to prevent the formation of tumor formation once a stem cell (e.g., a tumor stem cell) has been identified in adult tissue. Candidate agents can be screened, for example, in vivo in particular animal models (e.g., mammalian models, e.g., rodents such as, for example, mice or rats). Candidate anti-tumorigenic agents can be screened, for example, in clinical studies to discover if a trial regimen actually destroys the tumor stem cell component as opposed to the non-stem cell population that constitutes >99% of the cells in a tumor. With the process described herein candidate anti-tumor agents or tumor prevention agents can be screened in experimental animals using transplants from human tumors or tumors that arise de novo in experimental animals. Thus, agents that kill, slow or interfere with the symmetrical or asymmetrical divisions of cells with bell-shaped nuclei in cell culture would be recognized as candidates for tumor prevention or therapy in patients.

Alternatively, candidate agents can be screened in vitro or ex vivo (e.g., in cultured samples where nuclear morphologies are maintained). Methods for preserving tissues in primary cultures for extended periods of time are known in the art. Anti-tumorigenic agents can be identified in cultured samples where heteromorphic nuclear morphotypes are preserved. Thus, if such a cultured sample is treated with a candidate anti-tumorigenic agent and the prevalence of heteromorphic nuclear morphotypes is diminished, then the candidate anti-tumorigenic agent would be expected to be useful in treating tumors in patients in vivo.

The invention will be further described with reference to the following non-limiting examples.

EXAMPLE 1

Experimental Procedures

Sources of Cells and Tissues

All adult tissue and tumor specimens were obtained as surgical discards at the Massachusetts General Hospital through the Department of Pathology and the MGH Center for Cancer Research. Each tissue section was immediately placed in fresh ice cold fixative and transported to the MIT cytogenetics laboratory for further analyses. Use of the anonymous discarded sections had been approved by the Institutional Review Boards of both MGH and MIT. The fetal gut sections analyzed were not obtained for this research but were drawn from the archival slide collection of the Chernobyl Scientific Expedition charged with the task of discovering signs of genetic radiation damage in developing fetuses and children after the meltdown of the nuclear reactor at Chernobyl, Ukraine in 1985. Two normal adult colons that were discarded after surgery not related to cancer (five ~2-10 mm diameter polyps of two FAPC colons, four colon tumors, one pancreatic tumor and several independent colorectal metastases of the liver from two patients) were analyzed.

Tissue Excision, Fixation, Spreading and DNA Staining

The procedure uses fixed and stained tissue sections some 0.5 mm in thickness in which cellular adhesions are chemically disrupted to a degree that permits an orderly spreading of tissue on a microscope slide. This technique allows for the cells to retain the structural integrity of their nuclei. Small morphological structures such as stained nuclei and larger structures such as colonic crypts may still be observed albeit with some minimal distortion inherent in tissue spreading.

Nuclear morphotypes are visible especially where the colonic surgical discards are provided soon after resection (e.g., less than an hour after resection, more preferably, about or less than 30 minutes after resection). Sheets (~1 cm$^2$) of stripped colonic mucosa or 1 mm thick sections of adenomas, adenocarcinomas and/or metastases were placed immediately upon dissection into freshly prepared 4° C. Carnoy's fixative (3:1, methanol:glacial acetic acid). The volume of fixative is at least three times the volume of the tissue sample. Fresh fixative is replaced three times every 45 minutes for a total of three hours of fixation. Carnoy's fixative is then replaced by 4° C. 70% methanol and may be stored up to a year at approximately −20° C.

About 1 mm$^2$ pieces (length×width as distinct from section thickness) are excised from the whole fixed tissue sample for spreading and DNA staining. Each piece is rinsed in distilled water and placed in 2 mL of 1 N HCl at 60° C. for precisely 8 minutes for partial hydrolysis of macromolecules and DNA depurination. The hydrolysis is terminated by a rapid rinse in cold distilled water. The rinsed sample is steeped in 45% acetic acid (room temperature) for 15 to 30 minutes. This last step is known in botanical cytogenetics as "tissue maceration" that allows subsequent tissue cell spreading and observation of plant tissue sections with gentle pressure on microscope slides (Gostev, A. and Asker, S., 1978, *Hereditas*, 101: 98-104; Gostjeva, E., 1998, *Genetika*, 32:17-21). This "macerated" fixed tissue sample is used immediately for spreading on microscope slides. Each ~1 mm$^2$ macerated section is bisected to form two ~0.5×1 mm pieces of fixed, macerated tissue. Each piece is transferred into ~5 μL of acetic acid on a clean microscope slide and covered with a 22×22 mm cover slip. Holding the cover slip by the edges slight pressure is applied on the tissue sample to locate it in the middle of the slide.

For the spreading step, 5 layers of filter paper are folded and placed on the cover slip taking extreme care not to move the cover slip. A tweezer handle is moved steadily in one direction along the filter paper covering the cover slip with slight and even pressure. "Slight" means markedly less pressure than used in chromosome "squashes". The quality of the spreading is checked using a 20× phase contrast objective for each individual sample. An indication of a good colonic tissue spread is that there are no damaged nuclei on the edges of the whole tissue spread while crypts are pressed into what is essentially a monolayer preserving the morphological integrity of the crypts. Each well spread sample slide is placed immediately on a dry ice surface. In 2 minutes, when the spread tissue sample is completely frozen, a razor blade is inserted under one edge the cover slip that is gently lifted off. Slides are allowed to dry in a dust free environment for not less then one hour.

Staining procedures are performed at room temperature. Slides are placed in Coplin jars and filled with Schiff's reagent (Art. 9033, Merck) to stain the partially depurinated DNA of the nuclei. Slides are immersed in staining solution for one hour, rinsed in the same Coplin jar two times in 2×SSC (trisodium citrate 8.8 g/L, sodium chloride 17.5 g/L), once for 30 sec and once quickly. Slides are then rinsed with distilled water. The slides at this stage are suitable for observation of the distribution of DNA in nuclei including measurement of Feulgen DNA amounts in nuclei or condensed chromosomes by quantitative image analysis (Hardie, D. et al., 2002, *J. Histochem. Cytochem.*, 50:735-749).

To achieve superior resolution and imaging of interphase nuclei slides may be further stained with Giemsa. Immediately after rinsing in 2×SSC slides are placed in 1% Giemsa solution (Giemsa, Art. 9204, Merck) for five minutes then rinsed quickly first in Sörenssen buffer (disodium hydrogen phosphate dihydrate 11.87 g/L, potassium dihydrogen phosphate 9.07 g/L) and then distilled water. Water drops are shaken off the slide as if one were shaking a thermometer to avoid erosion of the stain. The slides are placed in a dust free environment to dry at room temperature for one hour. They are then placed in a Coplin jar filled with Xylene for at least 3 hours to remove fat. Cover slips are glued to the slides with DePex mounting media and permitted to dry for 3 hours at which time they are ready for high resolution scanning.

Microscope and Image Processing System

A KS 400 Image Analysis System™, Version 3.0, (Zeiss, Germany) was used to observe and record images for future quantitative analyses of nuclear dimensions and DNA content. The system consists of a motorized light microscope, Axioscope™, color CCD camera, AxioCam™ (Zeiss, Germany) linked to a personal computer. Images were transmitted from the microscope at 1.4/100 magnification of the planar apochromatic objective using visible light and 560 nm (green) filter when Feulgen stain alone was employed. No filter was used when Feulgen-Giemsa staining was employed. The frame grabber and optimal light exposure were adjusted prior to each scanning session. Nuclear images were recorded at a pixel size 0.0223×0.0223 um. Scanning parameters such as magnification, resolution and light exposure were saved to permit reproducible scans of the same slide.

EXAMPLE 2

Detection of Bell-Shaped Nuclei

Fetal Hindgut

Observations described herein are from two independent fetal gut sections are shown in FIGS. 1, 2A-2C and 3A-3F. Three observations were made. First, there was the array of seven distinct nuclear morphotypes summarized in FIG. 1. Secondly there was the orderly linear head to toe arrangement of bell-shaped nuclei organized in long (~20 to 50 micron diameter) tubes as shown in FIGS. 2A-2C. Thirdly, there were the extraordinary forms of symmetrical and asymmetrical amitoses involving bell-shaped nuclei as shown in FIGS. 3A-3F.

Phase contrast images (left frame, FIG. 2B) and stained nuclear images (middle frame, FIG. 2B) of the identical hindgut section when overlaid (right frame, FIG. 2C) showed that the a linearly oriented nuclei were contained in a previously unreported tube like structure which is itself about 20 50 microns in diameter. 280× magnification of the nuclei (middle frame, FIG. 2B) shows that these non spherical nuclei appear to be in the form of cups or bells. Higher resolution images (1400×) of nuclei in linear array shows them to have a reproducible bell shape that is apparently hollow. The "head to toe" orientation of the bells was preserved in all embryonic tubes observed but tubes snake backwards and forwards such that parallel tubes may have locally anti parallel orientation of bell-shaped nuclei.

Figure 3B:
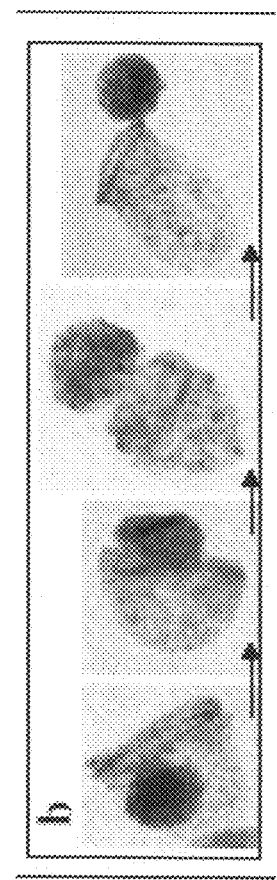
FIGS. 3A-3F show amitoses of bell-shaped nuclei embryonic gut.
Figure 3A:
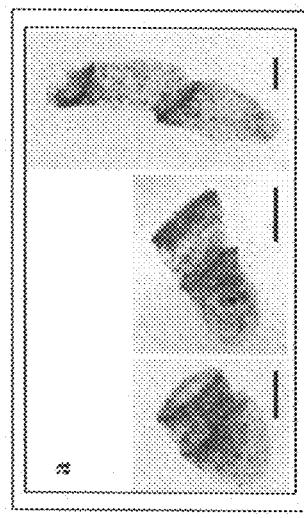
Figure 3F:
Figure 3E:
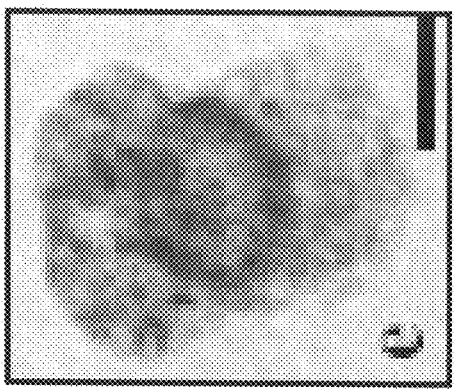
Figure 3D:
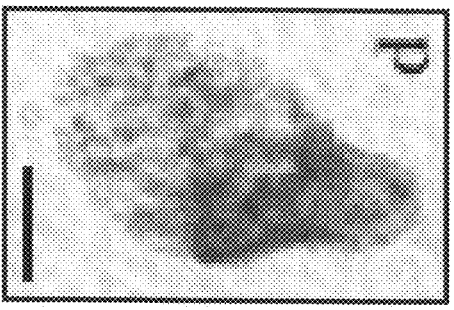

Bell-shaped nuclei were observed undergoing symmetrical or asymmetrical amitoses only within the tube-like structures. Symmetrical amitoses of bell-shaped nuclei resembled a simple separation of two stacked paper cups. At the highest resolution, the upper lip of these bells in division appeared to have a pair of condensed or partially condensed chromatids (see FIG. 1, arrows) encircling perhaps ¾ths of the bell's outer rim, as seen in FIGS. 3A and 3B. A variety of different bell shapes were found within the various tubes and these morphological variations were faithfully reproduced in symmetrical amitoses, FIG. 3A.

Figure 3C:
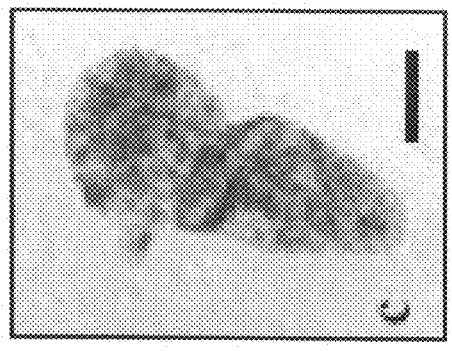
Figure 4C:
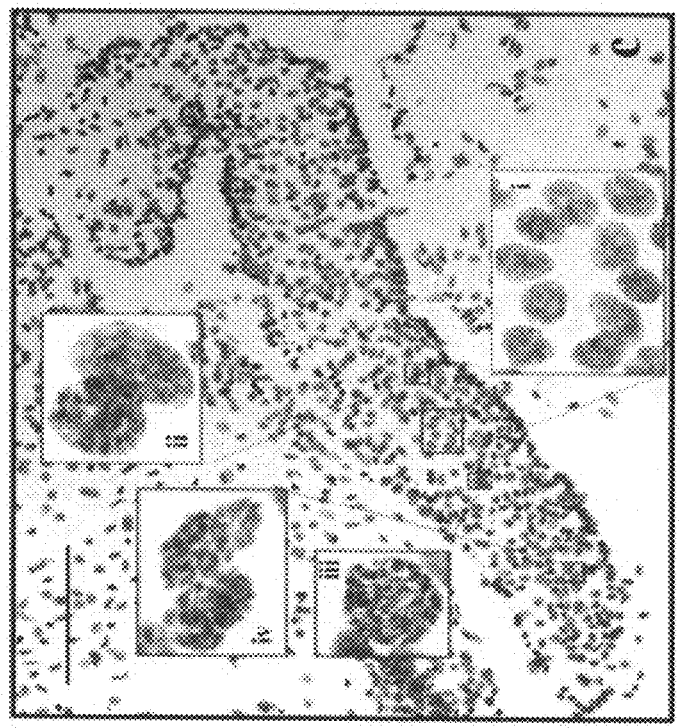
FIGS. 4A-4C show normal adult colonic crypts.
Figure 4B:
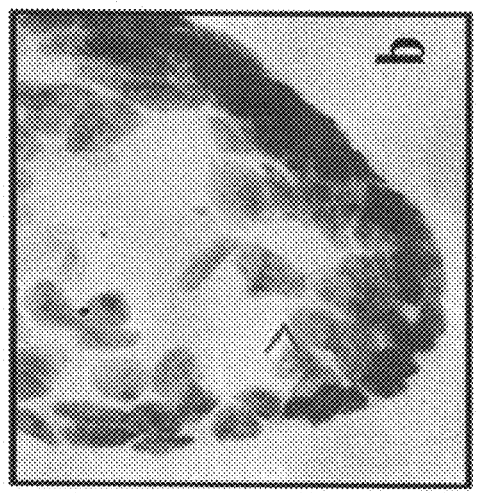
Figure 4A:
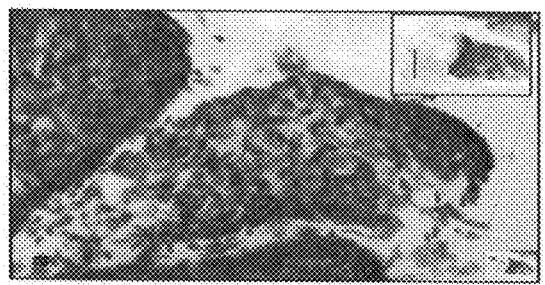

This previously undiscovered form of amitotic nuclear division of bell-shaped nuclei was, of course, surprising. But the fetal sections had more surprises than this. Throughout the gut sections bell-shaped nuclei within tubular structures were found apparently "giving birth" to nuclei. Examples of every form of nuclear shape found in the fetal sections and shown in FIG. 1 were found emerging from bell-shaped nuclei. These extraordinary amitotic asymmetrical forms of nuclear division are shown in FIG. 3C.

With regard to the nuclear morphotypes other than bell-shaped, all appeared to undergo mitoses forming local colonies of identical nuclear morphotypes. These mitotic divisions always occurred outside of the long tubes containing bell-shaped nuclei. Curiously, the specific nuclear morphology was preserved in prophase, and even recreated by association of the chromosomes in late anatelophases, as is also shown in FIG. 1.

Normal Colonic Epithelium

The combination of ~0.5 mm sections, the tissue maceration (see below) and gentle spreading combined with the DNA-specific staining to create particularly clear images of nuclei permitted recognition of three dimensional features. All, or nearly all, nuclei in crypts could be observed from the crypt base to the luminal surface. Many crypts either fractured or spread in such a way that individual nuclear shapes could be discerned. Cells with ovoid or spheroid nuclei line the crypt from just above the base to the epithelial extension into the lumen. However, in the first ~25 cells of the crypt base itself a nuclear morphotype that may be characterized as "discoid" (~2 3 microns thick and ~10 microns diameter) predominated. In less than 1% of crypt bases in which the cells were well separated a bell-shaped nucleus was discerned among the discoid nuclei. A similar low frequency of bell-shaped nuclei has been observed in preparations of adult liver. In an adult colon without any indication of neoplasia or pre-neoplasia no other nuclear morphological variant was observed in a cell by cell scan of about 800 well spread crypts.

Adenomas

Figure 5C:
FIGS. 5A-5E show enlarged images of adenomas.
Figure 5E:
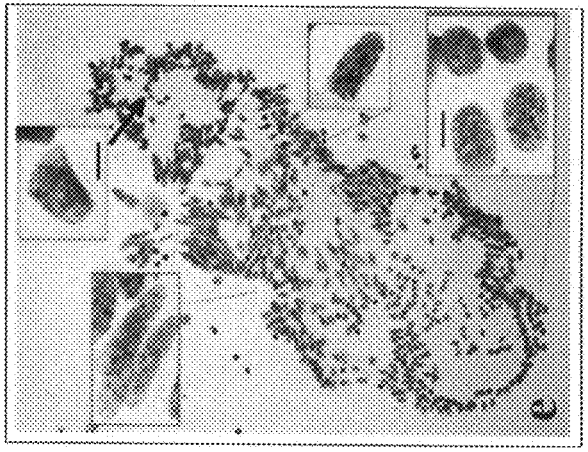
Figure 5D:
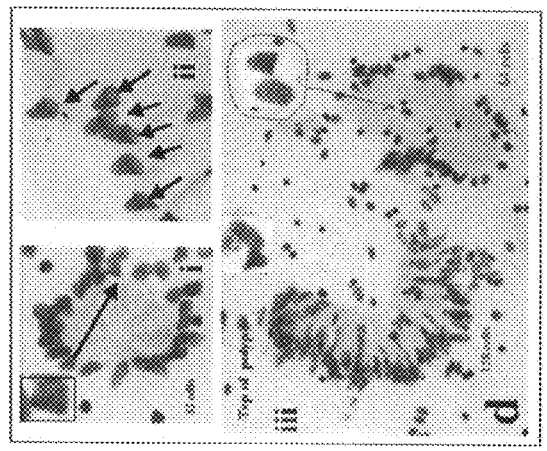
Figure 5A:
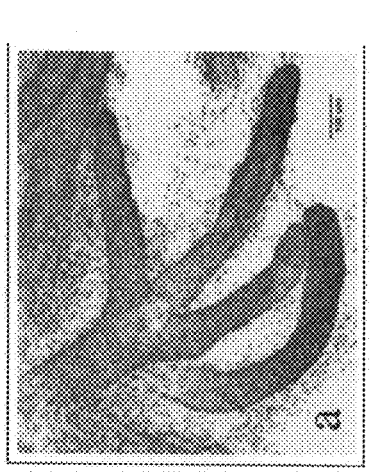
Figure 5B:

The adenomas contained many crypts, indistinguishable from normal colonic crypts, each with ~2000 cells. These were frequently found in branching forms as shown in FIG. 5A. The same spheroid and ovoid nuclei were present in the crypt walls, as in the normal colonic crypts, but frequently displayed one or two bell-shaped nuclei in the crypt base. Irregular crypt like structures were also observed containing up to ~8000 cells, which were more easily spread by tissue maceration (FIG. 5B). In addition, many diverse cells and groups were interspersed among the crypts and crypt like structures (FIG. 5C). Some structures appeared to be growing toward full-sized normal crypts containing ~250, ~500 or ~1000 cells (The spreading technique employed generally permitted exact cell counts in structures of up to several hundred cells.). Many cell groups were seen as "rings" of exactly 8, 16, 32, 64 and 128 cells each. (FIG. 5D). Higher magnification examination revealed that while most of the cells of the walls of the crypt like structures had spherical or oval nuclei as in the normal adult colonic crypt, colonies of cells with either oval, cigar-shaped or bullet-shaped nuclei appeared at crypt wall breaches. Colonies with oval and cigar shaped nuclei had been observed in fetal gut but the "bullet-shaped" nuclear morphotype was seen only in adenomas and adenocarcinomas (FIG. 5E).

The "bullet-shaped" nuclear morphotype also appeared to arise from bell-shaped nuclei by asymmetrical amitoses with the irregular end ("bitten off") emerging first. Small colonies of cells with bullet-shaped nuclei were seen and these colonies contained cells undergoing ordinary mitoses save for the interesting fact that the curious nuclear morphology was retained from early prophase through anatelophase.

While rare in the normal adult colon the bell-shaped nuclei were obviously playing an important role in adenomas. They appeared in a number of adenoma contexts. Some were found as one to ten or more "bells" in the spaces among the crypt like structures as shown in FIG. 5D. Others were found as single "bells" in multicellular ring structures in which one bell nucleus was always seen in the ring with 2n−1 cells of spherical or other morphology as in FIGS. 5C and 5D. In the smaller to full sized structures that cohered under spreading conditions as did normal colonic crypts, bell-shaped nuclei appeared as single bells, more often as a pair of bells or occasionally 4 or 8 bells within the crypt like structures basal cup. In the much larger irregular crypt like structures, bell-shaped nuclei were anatomically integrated into the walls of the aberrant structures mixed with cells of other nuclear morphologies. It appeared as if these larger irregular crypt like structures were mosaics of multiple different kinds of clusters each with it's own nuclear morphotype.

The bell-shaped nuclei of the adenomas differed in another remarkable way from the other nuclear morphotypes and from bell-shaped nuclei in embryos: though just more than a thousand bell-shaped nuclei have been observed in individual adenomas not a single bell-shaped nucleus in any adenoma has been observed in the symmetrical amitotic form found in fetal sections. It is also notable that no bell-shaped nucleus in a condition that could be described as pyknotic was observed among the adenomas scanned. Nuclei of all other morphological forms were frequently found in mitosis or pyknosis at roughly equal frequencies (about 1 5/1000 total nuclei) when whole sections were scanned. Small subsections varied greatly with regard to mitotic and pyknotic counts. As used herein, "pyknotic" refers to a condition of nuclear rupture and chromatin condensation in irregular clumps that is indicative of a dying cell.

Adenocarcinomas

Figure 6B:
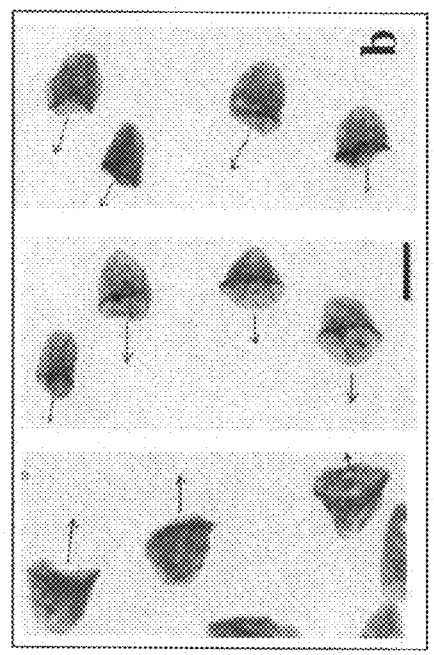
FIGS. 6A-6C show enlarged images of adenocarcinomas.
Figure 6C:
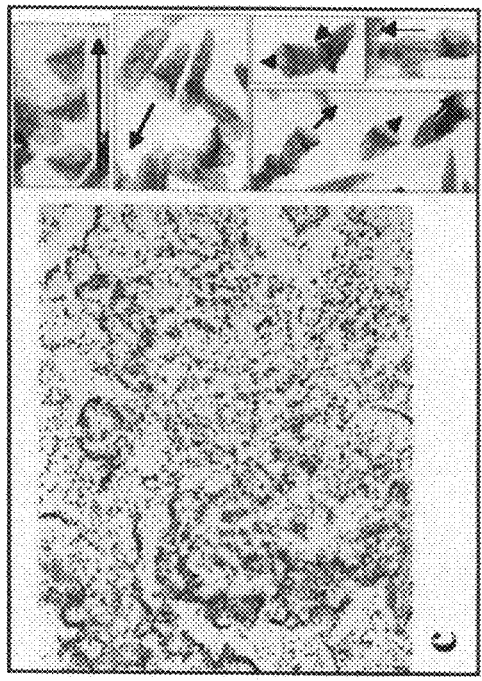
Figure 6A:
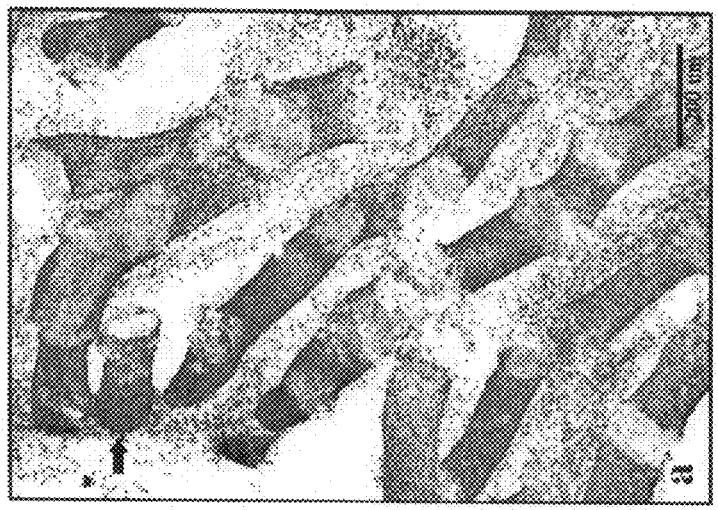
Figure 7A:
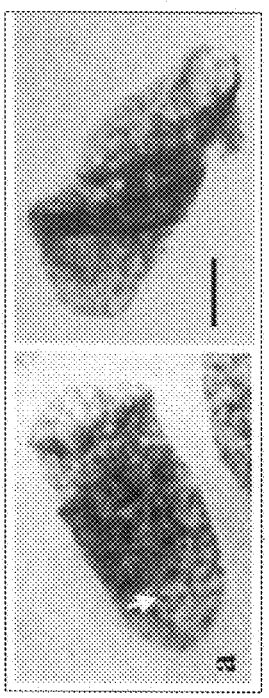
FIGS. 7A-7E are enlarged images depicting amitoses in adenocarcinomas.
Figure 7B:
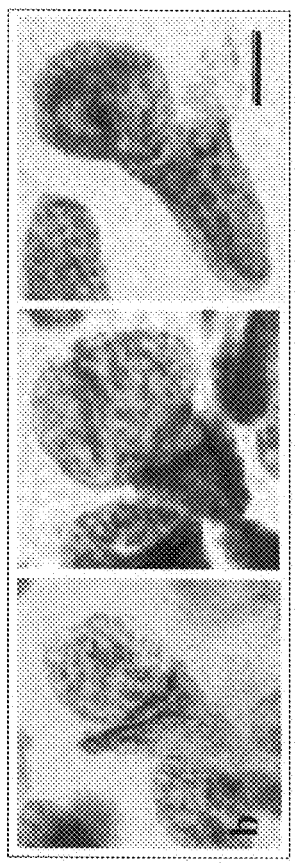
Figure 7C:
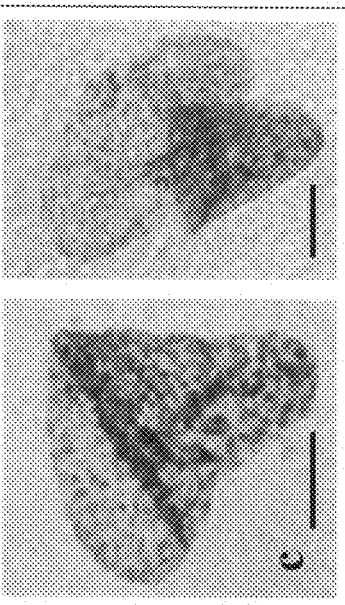
Figure 7D:
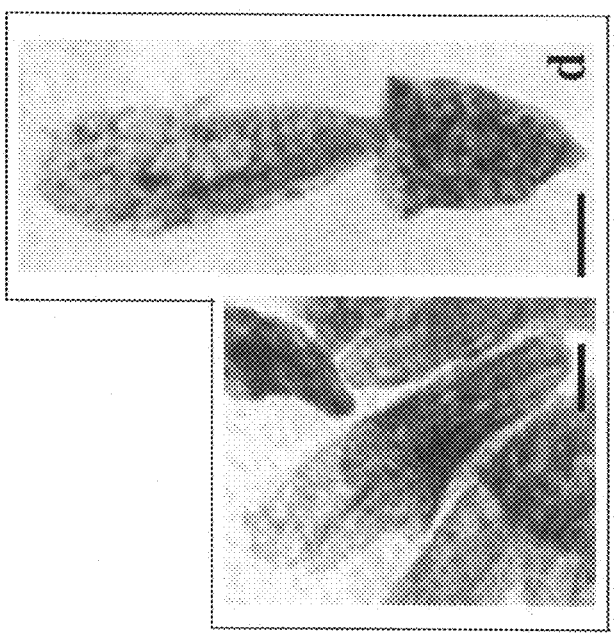
Figure 7E:
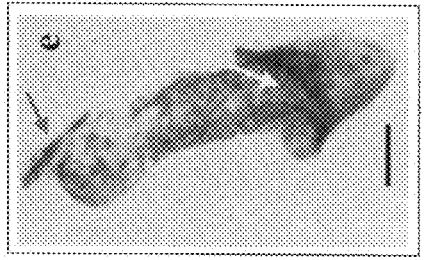

While adenocarcinomas had much greater masses and many individual sections resisted spreading by gentle pressure, the admixture of crypts, larger irregular crypt like structures and inter crypt presence of rings of 16, 32, 64 and 128 cells was essentially the same as in the much smaller adenomas. Breaches in the walls of the crypt like structures were associated with colonies of cells with identical nuclear morphologies persisting into the three dimensional distributions of condensed prophase chromosomes. Bell shaped nuclei were still found as singlets, pairs or larger numbers in the basal cup of crypts and embedded in complex whorls in the walls of the larger aberrant crypt like structures. FIGS. 6A-6C show a series of these bell-shaped nuclei all typical of what is seen in adenocarcinomas. The set of nuclear morphotypes in the adenocarcinomas appear to be identical with the set seen in adenomas. In particular the "bullet shaped" nuclear morphotype not observed in fetal sections or adult colons was frequently observed.

A discernible difference between adenomas and adenocarcinomas was that the orientation of the crypt like structures was haphazard with base to lumen directions apparently randomly oriented with regard to the tumor surface. Also crypts and irregular crypt like structures were not found frequently in the tumor interior, which may be better characterized as an eclectic but not chaotic collection of smaller, locally organized structures. It is possible that these interspersed colonies of cells with different nuclear forms represent a symbiotic community.

An important characteristic by which the adenocarcinomas differed from adenomas was the frequent appearance of apparently organized groupings of hundreds of bell-shaped nuclei, many of which were frequently (~1%) involved in symmetrical amitoses. At low magnification these appeared in the spaces among crypt like structures and looked like a spider web or leaf vein skeleton. At higher magnification the thin "veins" were found to be partially ordered strands of cells with bell-shaped nuclei having the curious characteristic of having their "mouths" oriented in the same direction, 90° from the axis: the shoulder-to-shoulder orientation (FIG. 6C). Furthermore, scanning through multiple sections of adenocarcinomas uncovered bell-shaped nuclei in the "head-to-toe" orientation observed in the fetal gut but not in the adenomas. These linearly arrayed nuclei were also encased in the tubular structure (syncytium) seen in the fetus. An occasional pyknotic figure that might have been a bell-shaped nucleus was observed but at a much lower frequency than symmetrical amitoses among bell-shaped nuclei.

Further Observations

Metastases of colorectal tumors in the liver recreate the pattern of nuclear morphotypes, crypts and crypt like structures seemingly indistinguishable from adenocarcinomas. Scanning sections of sections of adult human liver has revealed occasional bell-shaped nuclei as were observed in adult colonic crypts. Scans of adult mouse colons similarly revealed cells with bell-shaped nuclei in crypt bases as in adult humans. In a potentially important observation for growth and study of cultured cells with bell-shaped nuclei, a low frequency, ~1/10,000 cells, have been found in mouse cell cultures in which stem like behavior has been postulated and studied with regard to symmetrical and symmetrical cell division kinetics (Sherley, J. et al., 1995, *Proc. Natl. Acad. Sci. USA*, 92:136-140; Merok, J. et al., 2002, *Cancer Res.*, 62:6791-6795).

EXAMPLE 3

Organogenesis and Carcinogenesis

Post embryonic organizing stem cells of the fetal colon were specifically identified by an opened mouth, bell-shaped nuclear morphotype. These peculiar nuclei undergo both symmetric and asymmetric nuclear fission without general chromosome condensation. Nuclear fissions drive net growth and differentiation throughout fetal, neonatal and juvenile life before a final metamorphosis into adult maintenance stem cells. These bell-shaped nuclear morphotypes are rarely found in adult colonic crypt bases but reappear prominently in pre-neoplasia and neoplasia and appear to drive net growth and differentiation in colon adenomas, adenocarcinomas and metastases.

Combining these observations with inferences derived from analyses of historical age specific colorectal cancer rates, present day age specific colonic adenoma prevalence and direct measurements of genetic change in human tissues suggests a default hypothesis for late onset carcinogenesis in the colon and perhaps other sites: oncomutations required for tumor initiation occur at markedly higher rates in juvenile stem cells than in adult maintenance stem cells because of their peculiar DNA biochemistry and mode of segregation. The higher juvenile mutation rates have the effect of limiting tumor initiation events to the juvenile years. Initiated juvenile stem cells continue to create local patches of juvenile tissue eventually observed in the colon as polyps and these cells maintain the "mutator" phenotype imputed to juvenile cells. Additional oncomutation(s) and/or local biochemical conditions during the slow but inexorable growth of the pre-neoplastic colony switch one of the pre-neoplastic "juvenile" stem cells to a fetal stem cell phenotype that rapidly creates a lethal tumor mass.

Organogenesis

The idea that organogenesis is accomplished by a linear cascade of stem cells capable of net growth by self propagation in symmetrical divisions and responsible for differentiation by asymmetric divisions giving rise to a stem cell and an alternate cellular form is generally held by developmental biologists. Confusion arises when attempts are made to differentiate the identities and functions of the various forms and potentials of cells from the early embryonic stem cells of the blast cyst capable of giving rise to viable embryos on transplantation and stem cells such as those isolated from the bone marrow of animals capable of repopulating an hematopoietic system and possibly other organs. Adult stem cells or maintenance stem cells are posited to be responsible for repopulation of the many tissue elements that turn over in organs such as the colon. In adults one may imagine small depositories of stem cells capable of repopulating tissues and organs on demand. One can also imagine a different form of adult maintenance stem cell that defines clonal turnover units by intermittent asymmetrical divisions that produce an initial transition cell that is lost by subsequent binary divisions to secondary transition cells up to differentiated terminal cells.

Disclosed herein are structures containing easily identifiable nuclear forms that appear to undergo both symmetric and asymmetric nuclear fission. These forms are identified by their bell-shaped nuclear morphotypes that comprise some 30% of all nuclei of human gut in 5-7 week fetuses but are found in the basal apex in somewhat less than 1% of adult colonic crypts.

Carcinogenesis

The idea that carcinogenesis is accomplished by a linear cascade of stem cells capable of net growth by self propagation in symmetrical divisions and responsible for differentiation by asymmetric divisions to create the heterogeneity evidenced in adenocarcinomas is less widely held. The concept of carcinogenesis as "loss of cellular control" accompanied by seemingly random expression of genes such as those expressed in early embryogenesis is fairly widespread. However, dilution and transplantation experiments, similar to those demonstrating the physical existence of organ restoring stem cells in hemoleukopoiesis have established the existence of a very small fraction of tumor cells having the ability to give rise to a growing tumor containing a variety of cell types. These practical demonstrations of the existence of tumor stem cells requires reflection on the idea of cancer as a highly degenerate state and probing the possibility that it, like organogenesis, is the expression of specific changes that define a pathway from normal stem cells to tumor stem cells. Relevant to this line of thought is the finding of bell-shaped nuclei identical to those found in colonic embryogenesis in both colonic polyps (adenomas, pre-neoplastic lesions) and tumors (adenocarcinomas, neoplasia) and subsequent metastases. Preliminary enumeration of these nuclear forms and their frequency of symmetrical nuclear divisions permit comparison to the expected low division rates of pre-neoplasia and rapid division of neoplasia.

Relationship of Stem Cell Biology to Age Specific Cancer Rates

It is reasonable to infer the hypothesis that initiated stem cells grow at near juvenile rates to form a pre-neoplastic colony (adenoma, polyp) from which inexorably emerged a neoplastic stem cell that grows at near fetal rates to form a lethal tumor. The hypothesis that neoplasia is are expression of the fetal phenotype is not original with us being ascribed to mid 19th century pathologists such as Cohnheim. The hypothesis arises that pre-neoplasia, adenomas or polyps in the human colon is a simple continuation of the phenotype of the juvenile colon.

Data and derived inferences about the growth rate of pre-neoplasia were augmented by a fortuitous discovery about the growth rates of children's weights as a function of age: male and female juveniles increase in average mass exponentially with a doubling time of about 6 years from about 1.5 years to 14.5 years in females and to 16.5 years in males. The growth rate during these age intervals is 0.158 for males, 0.167 for females. Relating the growth rate of the colon to that of body mass required modeling of the surface area of a cylinder inside a growing sphere that would increase as the mass ⅔ or in this case, ~0.162/3~0.11, a value equal to that estimated for the colonic pre-neoplastic growth rate.

As the estimated growth rates of pre-neoplastic lesions of the colon are about equal to the estimated growth rate of the juvenile colon, the hypothesis developed that pre-neoplasia in some way recreated conditions of juvenile growth. As net growth of juvenile stem cells would presumably be required for juvenile tissue growth, the idea arose that adenomas, which contain many of the histological attributes of organized colon, might in fact be equivalent to patches of juvenile tissue expansion in a background of non growing adult crypts. This hypothesis has been tested by computations limiting the age of initiation to the age of maximum body mass and found that it is indeed possible to derive sets of parameters that accord with the age specific colorectal cancer rates if the process of initiation is limited to the juvenile period. Indeed, parameters can be derived that fit the cancer rate data if initiation is limited to age five or lower. Such calculations demonstrate that the hypothesis of limitation of initiation to within the juvenile period is consistent with the age specific cancer rate data but do not, however, demonstrate the hypothesis' validity.

Age Specific Detection of Adenomas

These theoretical constructs would remain in the domain of untestable hypotheses were it not for an important set of clinical observations that seem to bear directly on the hypothesis that tumor initiation is bounded by the juvenile period. In studies designed to define the optimal age and number of proctoscopic examinations to detect and remove potentially neoplastic colonic adenomas, the fraction of persons with adenomas detectable by flexible sigmoidoscopy was found to reach a stable maximum at about sixty years of age. When observations by proctologists with consistently high records of adenomas detection were analyzed, ~15% of males and some ~10% of females had somewhat more than one adenoma on average. From these clinical data, it is reasonable to infer: first, the slowly growing pre-neoplastic adenomas must have had their origins far earlier in life than age sixty (with a growth rate of 0.11 a tissue stem cell initiated at age 1 would have increased to only $2^7=128$ pre-neoplastic stem cells by age 63. The number of total cells in such an adenoma would be much larger on the order of a million total cells); second, the similarity between the fraction of males with polyps, ~15%, and the estimated minimum fraction of males (1890s cohort) at lifetime risk of colon cancer, 18-20%, suggests that the individuals with adenomas at age sixty and those at lifetime risk may be identical (if this inference is confirmed on further analysis it would be important for two reasons: (a) it would eliminate any role for inherited or genetic risk factors in the eventual transformation of pre-neoplastic lesions into neoplastic lesions in the colon, and (b) it would eliminate any important role for competing forms of mortality with risk factors shared with colorectal cancer); third, the appearance of an average of more than one polyp in persons with polyps implies the male population consists of a subpopulation of some 20% in whom tumor initiation and pre-neoplastic growth occur and a separate distinct subpopulation of some 80% in which either tumor initiation and/or pre-neoplastic growth do not occur; fourth, insofar as calculations of pre-neoplastic growth rates in males and females yield identical results, the male/female ratio of persons with polyps over age sixty with polyps and the gender differences in the average number of polyps/individual with polyps permits the hypothesis that gender differences in cancer rates may be ascribed entirely to the number of initiated colonic stem cells created through the initiation susceptible juvenile or pre juvenile years (for instance, if oncomutation rates were the same in males and females, the ratio of expected pre-neoplastic colonies created in the juvenile years would simply be the ratio of stem cell years experienced up to maturation at about 14.5 years in females and 16.5 years in males).

Histopathology

Throughout the 20th century, molecular, biochemical and histolopathological analytical methods have been applied in parallel but independent studies of tumors and embryos. Rich and extensive data obtained showed that many normal ontogenic characteristics associated with the growth and development of humans re appear much later in life as abnormal pathological growth that is cancers. At the beginning of 21st century scientists put forward the hypothesis that similarity between embryos and tumors (both monoclonal in origin, both appearing in explicit heterogeneity of cells populations) can be explained from a single point, that is the very specific cell such as a stem cell, can give rise to a whole embryo, organs and tissues of an embryo as well as of a large tumor. Said scientists have not distinguished as herein between an embryonic and a fetal stem cell.

Table 1 shows the stem cells hierarchy in early human development. Between gestational age of 4 weeks (the stage of blastocyst and gastrulation) and 5-12 weeks (the stage of organogenesis) there is a cascade of stem cells arising to correspond to each particular stage of early fetal development.

Table 1. The hierarchy of stem cells arising through onto-genesis and through "blocking" and "reversing" mutagenesis of a stem cells to become a cancer stem cells.

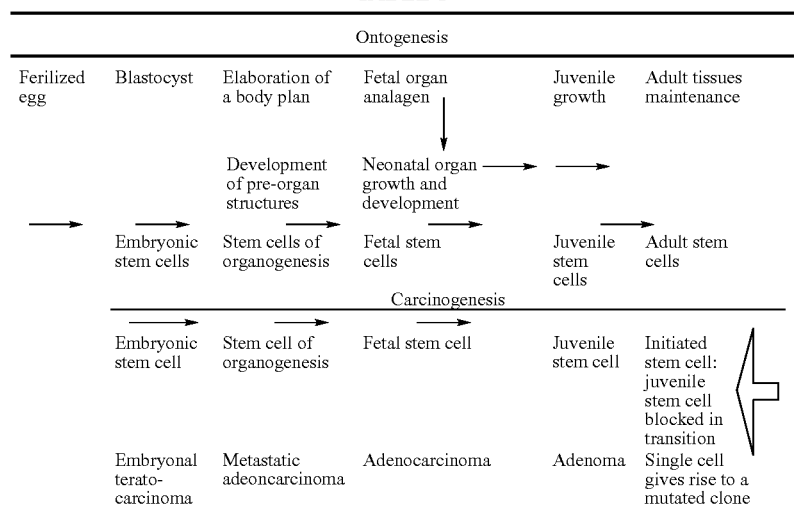

TABLE 1

The importance of distinguishing among ontogenetically different stem cells has come from the disclosed cytogenetic evaluations of human fetal and adult tissues.

Embryonic stem cells of epiblast are the cells that are not committed to anything in pre-implanted embryo, divide by mitosis and their nuclei are simply spherical in shape. They have no evidence of retainable polarity of the cell, nor of the nucleus. At the stage of elaboration of a body plan and organogenesis the cells acquire the polarity thought to be necessary to start spatially "directed" migration of cells and cell layers to create bilaterally symmetrical body of a human, to outline positions of internal organs in a body cavity.

Figure 8:
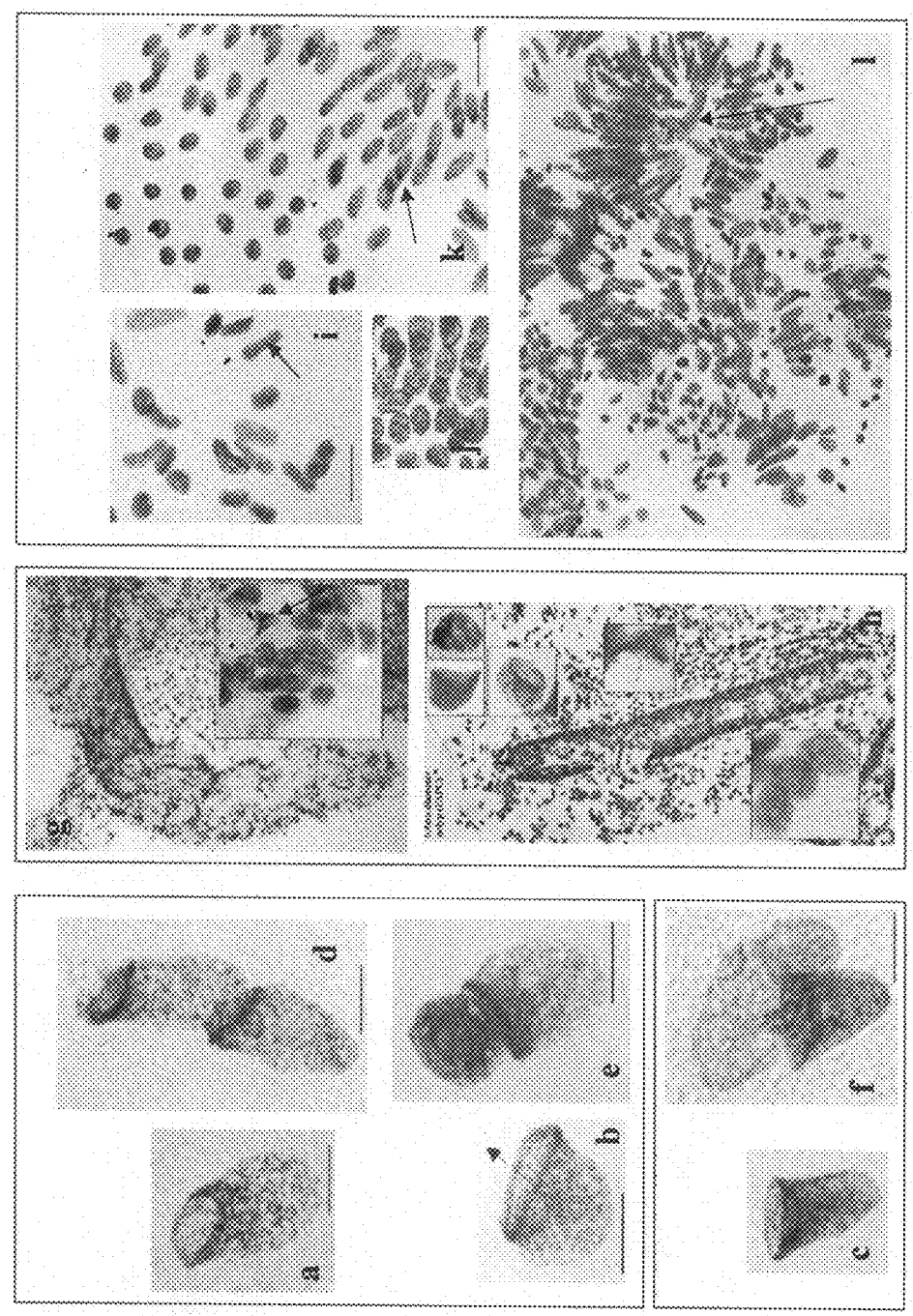
FIGS. 8(a)-(l) show Feulgen DNA stained nuclei of human colonic epithelium: a, b: the bell-shaped nuclei of gut; c: of colon adenoma; d: symmetrical nuclear fission of the bell-shaped nucleus in gut; e: asymmetrical nuclear division; f: asymmetrical nuclear fission (condensed spherical nucleus emerges from the bell-shaped nucleus) in colon adenocarcinoma; g: bell-shaped nuclei at the bottom of normal looking crypts (arrowed) and h: throughout 'incipient' crypt of adenoma; i: diversity of nuclei morphotypes in gut. The cigar-shaped nuclei arrowed in cell spreads obtained from adenoma (k) and colon adenocarcinoma (l). In 'j' the nuclei of spherical shape, typical for adult normal colonic crypts, are shown. The bar size is 5 µm.

The middle stage of organogenesis of a gut (5-7 weeks), from which all major parts of a digestive system will arise, includes cells comprising nuclei that are not just spherical but have diverse nuclear morphotypes. Nuclei of some of the cells have distinct polarity and divide not by mitosis but by the process more associated with "cup-from-cup" nuclear fission (FIG. 8). This particular observation has led to the conclusion that the stem cells of organogenesis could be quite different from that observed in blastomeres of an embryo.

In postnatal growth of a child and later of a juvenile the epithelial tissue continue to grow by multiplication of the stem cell to increase the number of turnover units per organ, and the number of cells per turnover unit until both features reach an organ-specific size maintained throughout life of an adult. For this matter, the stem cells taking over the growth and function of organs in juveniles should be distinguished from the stem cells of fetal growth and development as juvenile stem cells. If Sell's hypothesis of a 'relationship between the stage of differentiation of cancer stem cells and type of tumors' is correct, the ability to identify a single stem cell in its "adult", "juvenile", "fetal" or "embryonic" form would be a significant breakthrough in the analysis of quantitative and qualitative characteristics of cancers (Sell, S., 2004. Crit. Rev. Oncol. Hematol., 51:1-28). Technical tools to identify and collect a pure population of same type stem cells in a test tube are clearly useful.

Nuclei in the cells of developing fetal gut can be organized as a hollow bells (FIG. 8: a,b). Not only the cells with such nuclei are present at ~30% in the fetal gut but they have a very peculiar arrangement pattern in the gut tissue: nuclei are oriented in one direction as "bell upon the bell". They are also enclosed in the structures resembling tubular syncytia. In the normal crypts of adult colonic epithelium the cells with bell-shaped nuclei are rare and, if they are present, their number is not more than one per crypt. The cells with the same bell-shaped nuclei appear in adenomas in larger numbers, in every crypt, normal or aberrant one (see FIG. 8: g,h) and then reappear at high frequency in aberrant crypts and tumor masses of adenocarcinomas (see Table 1).

Cells with bell-shaped nuclei are observed in large numbers in fetuses, are rare in normal adult colon free of neoplasia, present, in small numbers (<1000) in adenomas of a few cubic millimeters and large numbers (>1,000,000) in adenocarcinomas of several cubic centimeters.

An argument that these cells could be stem cells have been supported by another, also unusual, observations of bell-shaped nuclei divisions. Within the tubular syncytia the bell-shaped nuclei were giving rise to amazingly identical 3D copy of themselves, as if a photocopy of a "template" object. All stages of consequential separation of the bell-shaped nuclei (as a separation of a two paper cups), referred to herein as "nuclear fission" because of the absence of nuclear condensation to form mitotic chromosomes and typical mitotic apparatus, have been detected (FIG. 8: d). This finding has been followed by the observations of all seven nuclear morphotypes previously found in developing human gut (FIG. 8: e,i) as emerging from the bell-shaped nuclear, always in one direction: out of the "mouth" of the bell. Cells with different nuclear morphotypes are phenotypically different and one can expect to detect the difference in gene expression and protein synthesis profiles between the cells with different nuclear morphotype.

The cells of an embryonic blastomere do not contain nuclei shaped as hollow bells; they have spherical nuclei and they are "embryonic stem cells". At the same time the hollow bell-shaped nuclei are already observed as early as ~5 weeks of gestation. The next stage in human life after fetal gut development where cells with bell-shaped nuclei reappear in large quantities is a pathological condition of adult colon: colon adenoma. An explicit diversity of nuclear morphotypes is also observable in colon tumors, very similar to one in fetal colon. The cells and nuclear morphotypes diversity is another reflection of cells "heterogeneity" in tumors. Tumors are also characterized by histopathologists as containing immature cells. At different stages in developing of a tumor a single juvenile stem cell in pre neoplasia and a single fetal stem cell in neoplasia can contribute to heterogeneous phenotype of both but with different fractions of immature cells (Table 2).

TABLE 2

Stem cells and their qualities in embryogenesis and carcinogenesis as observed in histopathological specimens of a colon.

| Stem cell qualities | In fetal 5-7 weeks gut | Adult normal tissue | Pre-neoplastic lesion (adenoma) | Adenocarcinoma |
|---|---|---|---|---|
| Differentiation status | The stem cells of organogenesis. | The adult stem cells | The juvenile stem cell | The stem cell of organogenesis |
| Tissue, organ specific number | High fraction (up to 30% in 5 weeks gut) | Low (~4 × $10^{-5}$) | Low but not as low as in normal epithelium (~2-4 × $10^{-3}$) | Relatively high (mean value ~0.2%) |
| Net growth rate | Expansion of different cells types in organogenesis | Maintenance of specific cells in adult crypt | First clonal appearance of the cells 'of fetal gut' type | Multiple clones of cells morphologically resembling those of fetal gut. |
| Multiplication and self-renewal by symmetric division | Frequently observed in fetal gut | Not observed | Not observed | Observed but more rare then asymmetrical types of divisions |
| Giving rise to a different cell lineages (asymmetric division) | Frequently observed in fetal gut | Not observed | Infrequent asymmetrical divisions observed | More frequent asymmetrical divisions observed |
| Cell and/or nuclear polarity | Distinct polarity of the nuclear is observable | The nuclei in crypts niches have 'single way' orientation | Orientation of the nuclei can differ throughout crypts | Probably defines an 'inward' invasive tumor's growth |

EXAMPLE 4

Methods of Characterization

Described herein are methods to characterize nuclear structures, DNA content and the spatial distribution of chromosomes in bell-shaped nuclei of cells and syncytia by quantitative image cytometry and/or confocal microscopy. These methods allow for the discovery of DNA content and/or chromosome distribution vary among bell-shaped nuclei of differing morphology, tumor type (colonic vs. pancreatic) and niches within tumors. They also allow for the characterization of the progress of DNA synthesis and presence of proteins associated with mitosis in bell-shaped nuclei during symmetrical and the several forms of asymmetrical nuclear fission.

Also described herein are methods useful in isolating cells and syncytia with bell-shaped nuclei as homogeneous samples. Such methods include the use of "catapult" pressure activated laser micro dissection to create samples of cells homogeneous for nuclear morphology that may be applied to analyses of metabolites and macromolecules Described herein is an exploration of how bell-shaped nuclei are spatially organized, how chromatin is dispersed in the nuclei, whether or not specific chromosomes occupy specific territories throughout the interior of nuclear lamina might suggest more specific therapeutic targets research and provide additional understanding of the relationship between nuclear morphotype (shape) and gene expression. Such exploration can be performed by existing methods of immunocytochemistry, molecular biology and related sciences.

Figure 9:
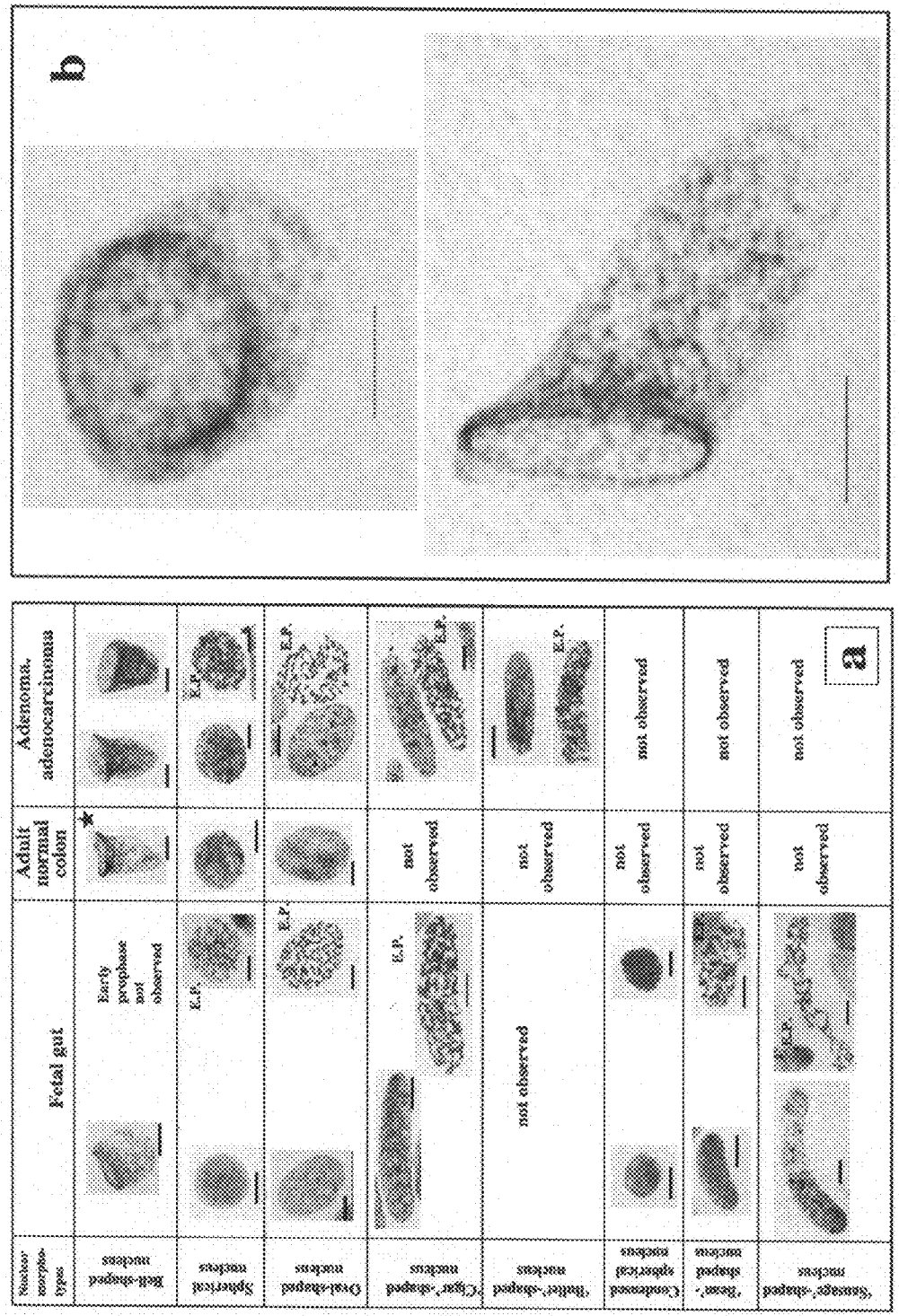
FIGS. 9(a)-(b) show a summary of key images. (a) Examples of nuclear morphotypes observed in interphase and early prophase (E. P.) cells in human fetal gut, normal colonic mucosa, adenomas and adenocarcinomas. (H-Bell-shaped nuclei are rarely observed in adult colon). (b) High resolution image (1400×) of bell-shaped nuclei of fetal gut. Condensed DNA appears to create an annulus that maintains an opening into the hollow bell structure. Scale bar, 5 µm.
Figure 12:
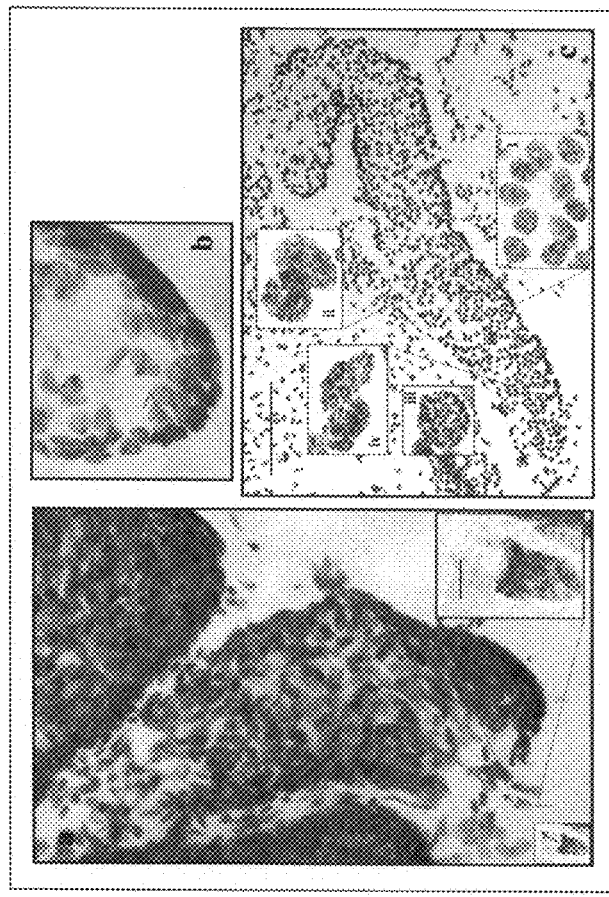
FIGS. 12(a)-(c) show normal adult colonic crypts: (a) Crypts of about 2000 spheroid, spherical or discoid nuclei occasionally (<1/100) contained a recognizable bell-shaped nucleus [arrow] located at the bottom of the crypt; (b) Crypt base showing another bell-shaped nucleus; (c) Morphotypes of interphase and mitotic nuclei of the walls and luminal surface in a well spread crypt. The enlarged images show: [i] spherical and oval interphase nuclei, [ii, iii] early prophases of spherical and oval shaped nuclei, and [iv] an anatelophase nucleus. Scale bars, 100 µm for low and 5 µm for high magnification images.
Figure 10:
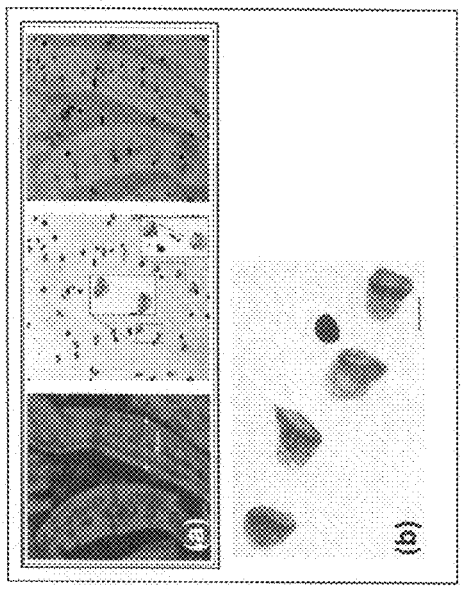
FIGS. 10(a)-(b) shows sections of embryonic gut, 5-7 weeks: (a) Phase contrast image (left frame) and stained nuclei image (middle) and the merged image (right) show the linear arrays of nuclei within ~50 micron diameter tubular syncytium; (b) High resolution image of the nuclei shows hollow bell-shaped structures. The head-to-toe orientation of the bells is preserved in all embryonic tubes observed but tubes snake backwards and forwards such that parallel tubes may have locally anti parallel bell-shaped nuclei orientation. Scale bars, 50 µm at low and 5 µm at high magnification.
Figure 11:
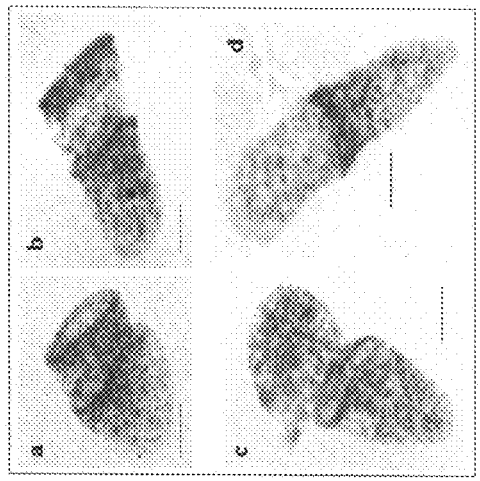
FIGS. 11(a)-(d) show nuclear fission of bell-shaped nuclei in fetal gut. a, b: Symmetrical nuclear fission: bell-shaped nuclei emerges from bell-shaped nuclei of similar shape. c,d: Asymmetrical nuclear fission: a spherical nucleus, and a cigar-shaped nuclei emerging from a bell-shaped nucleus. Scale bar, 5 µm.
Figure 14:
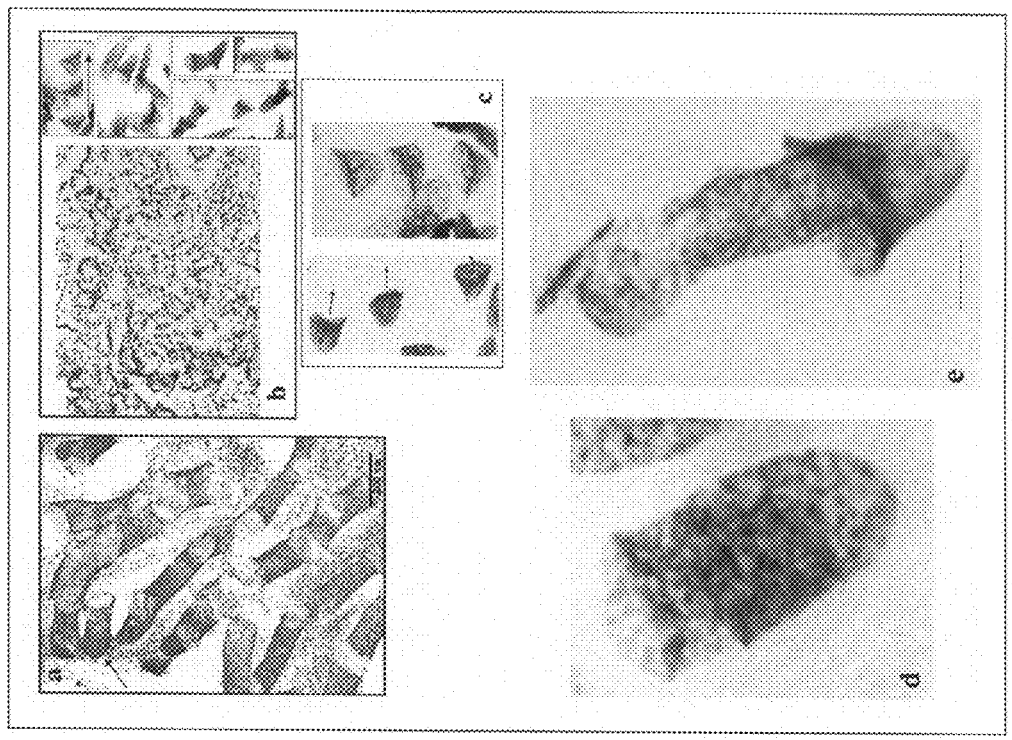
FIGS. 14(a)-(e) show adenocarcinomas. (a) Very large crypt like structures (>8000 cells), with branches with frequent break points. The arrow indicates an example of an ~250 cell crypt like structure found primarily near the surface of the tumor. (b) Interior tumor mass with multiple where multiple bell-shaped nuclei ($2 \times 10^{-3}$ of all nuclear morphotypes). (c) Bell-shaped nuclei in (b) oriented in head to toe syncytial and non-syncytial side by side configurations. (d) Symmetrical nuclear fission in adenocarcinoma. (e) Asymmetrical nuclear fission of a bell creating a cigar-shaped nucleus in adenocarcinoma. Similar structures have been observed in colonic metastases to the liver. Scale bar, 5 µm.
Figure 13:
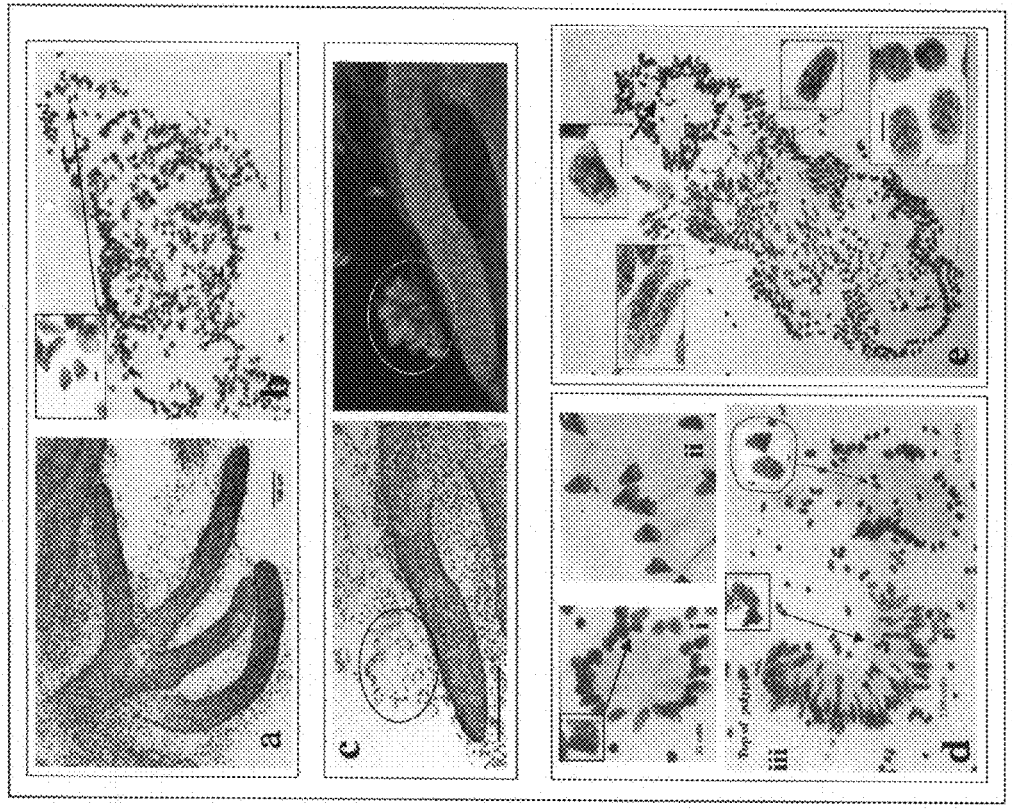
FIGS. 13(a)-(e) show adenomas. (a) Characteristic large branching crypt of adenomas. (b) An irregular crypt like structure found throughout adenomas. Typically two, but sometimes 1, 4 or even 8, bell-shaped nuclei (insert) appear at the base of these large (>4000 cell) irregular crypt like structures. (c) A cluster of cells of similar nuclear morphotype containing one bell-shaped nucleus. These forms of clusters contain exactly 16, 32, 64, and 128 total cells. Left panel, Feulgen Giemsa stain. Right panel, phase contrast fluorescent image. (d) Contexts in which bell-shaped nuclei appear in adenomas: (i) Cluster with 31 ovoid nuclei and one bell-shaped nucleus, (ii) Multiple bell-shaped nuclei in shoulder to shoulder arrangement, (iii) Bell-shaped nuclei arranged in a side by side pattern (arrow) (iii) Irregular mixture of ~250 nuclei of with several bell-shaped nuclei suggestive of nascent crypt bases. (e) Irregular crypt-like structure containing apparently clonal patches of cells of 5 different nuclear morphotypes with one bell-shaped nucleus [arrow] at the base. Scale bars, 100 µm (in 'a,b') and 5 µm (in 'e').
Figure 15:
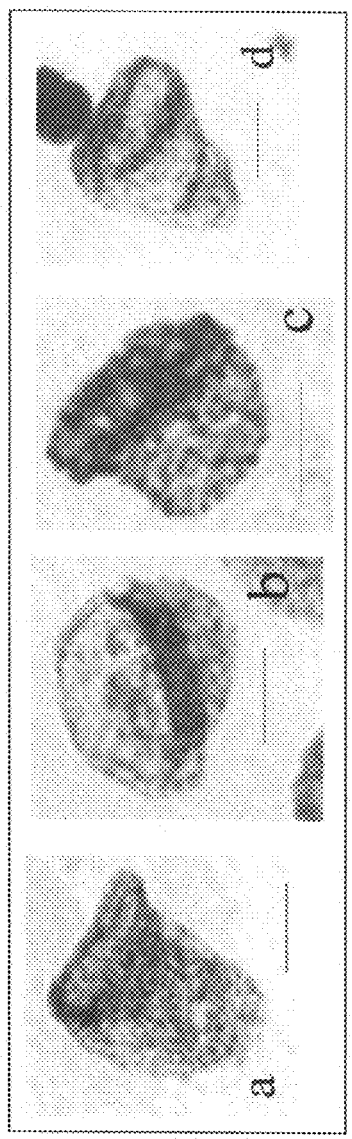
FIGS. 15(a)-(d) show morphological similarity of bell-shaped nuclei (Feulgen DNA stained in purple) as revealed in human tissues of: (a) embryonic gut, (b), colonic adenocarcinoma, (c) liver metastasis of colonic tumor, (d) pancreatic tumor. Condensed chromatin streak seen in lower half of bell in 'd' is seen in all bell-shaped nuclei from pancreatic but not at all in colonic tumors. Bar scale, 5 µm.
Figure 16:
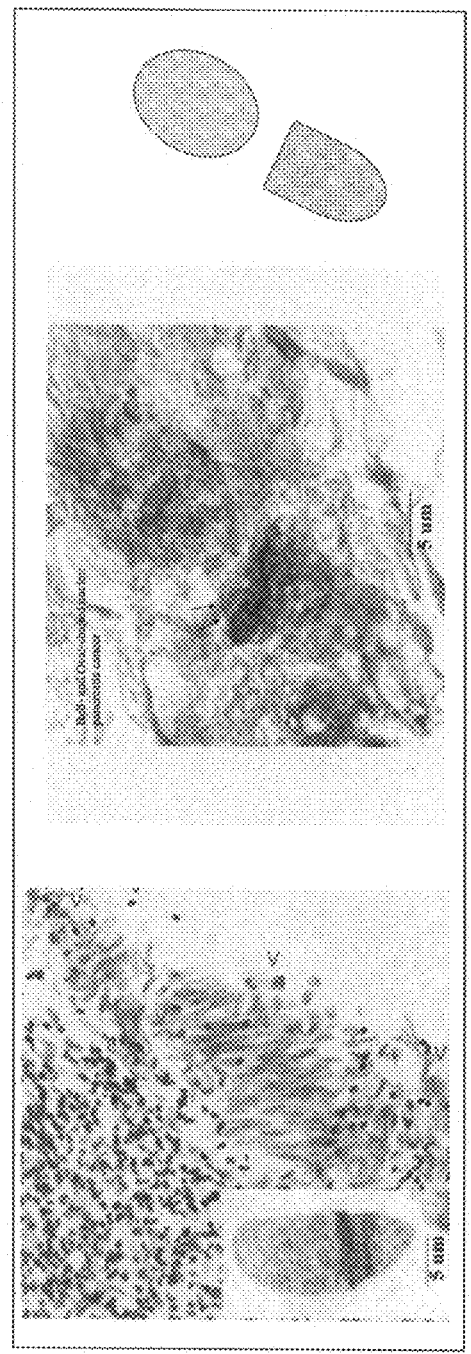
FIG. 16 shows bell-shaped nuclei detected readily by the histological procedure disclosed herein (Feulgen stain) and rarely (only example as yet) by standard histological procedures creating microtome sections of 5 microns sections (hematoxylin and eosin stain (H&E)). Same tumor, fixation within 30 minutes of resection: Left panel: the bell-shaped nuclei giving rise to cigar shaped nuclei (100× magnification image to the left) present as a colony at the edge of a pancreatic tumor containing a number of asymmetrically dividing cells (arrowheads). Middle panel: the single example found to date of bell- and oval-shaped nuclei visible on a standard tissue section slide in juxtaposition suggesting a recent asymmetrical nuclear division. The bell-shaped nucleus appears to have chromatin strands still attaching it to the oval nucleus (arrows). Right panel: cartoon of the original picture showing this interpretation.
Figures 17, 18:
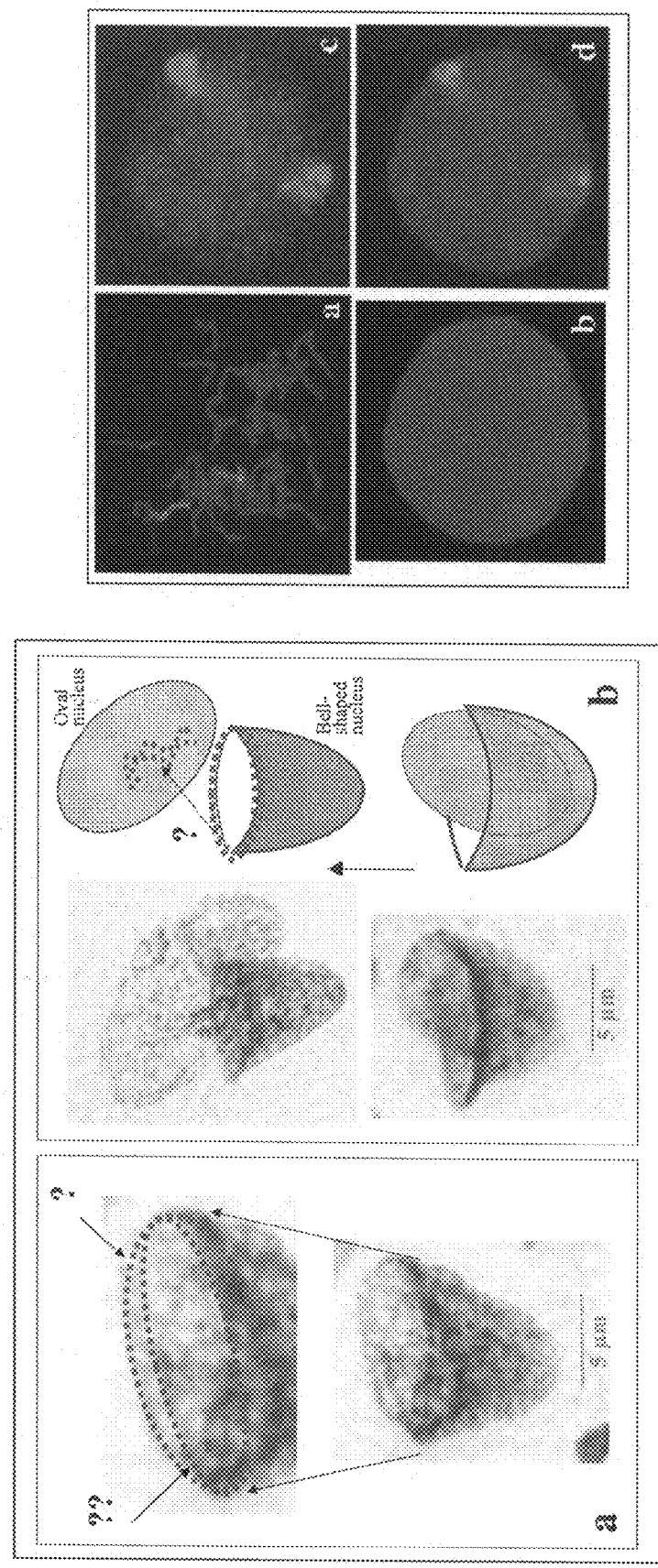
FIGS. 17(a)-(b) is an illustration of a 'target of interest' in application of FISH to explore non-dividing and dividing bell-shaped nuclei in tumors: (a) Chromatin, stained darker because of higher concentration of DNA per square micron in the nucleus, creates the unique structure as a part of bell-shaped morphology, resembling prophase chromosomes arranged as two parallel circles. These circles put into drawing (above) illustrate the prediction of that specific chromosomes might be found at this specific site of bell-shaped nuclei in colon tumors, (b) Chromatin distribution and specific chromosome positioning changes as imaginary transformation (bell- to oval-shaped nuclei here) taking place throughout asymmetrical division of the bell-shaped nuclei.
FIGS. 18(a)-(d) show the results of fluorescent in situ hybridization of chromosome 11 in spherical nuclei of TK 6 human cells. (a) two pairs of chromosomes in prophase chromosome spreads, (b) spherical nuclei DAPI nuclear stain, (c) same chromosome pair hybridized with FITC fluorescence probe, (d) merged image of DAPI and FITC interphase chromosomes stain.
Figure 19:
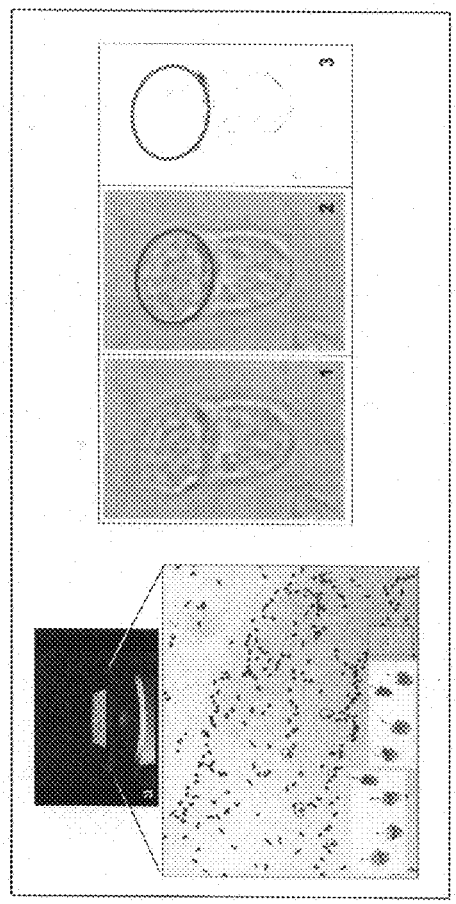
FIG. 19 shows bell-shaped nuclei as 'targets' in collection by laser pressure catapulting system ("laser pressure microdissection"): upper left panel: The microscopic slide with cell spreads positioned in front of pulsed UV A laser that is coupled to a microscope. Lower left panel: single nuclei can be seen through a microscope as shown for the cells spread of colon tumor tissue with bell-shaped nuclei in vision; Right panel: Same nuclei with recognizable morphology of the bell in non-stained slides.
Figure 20:
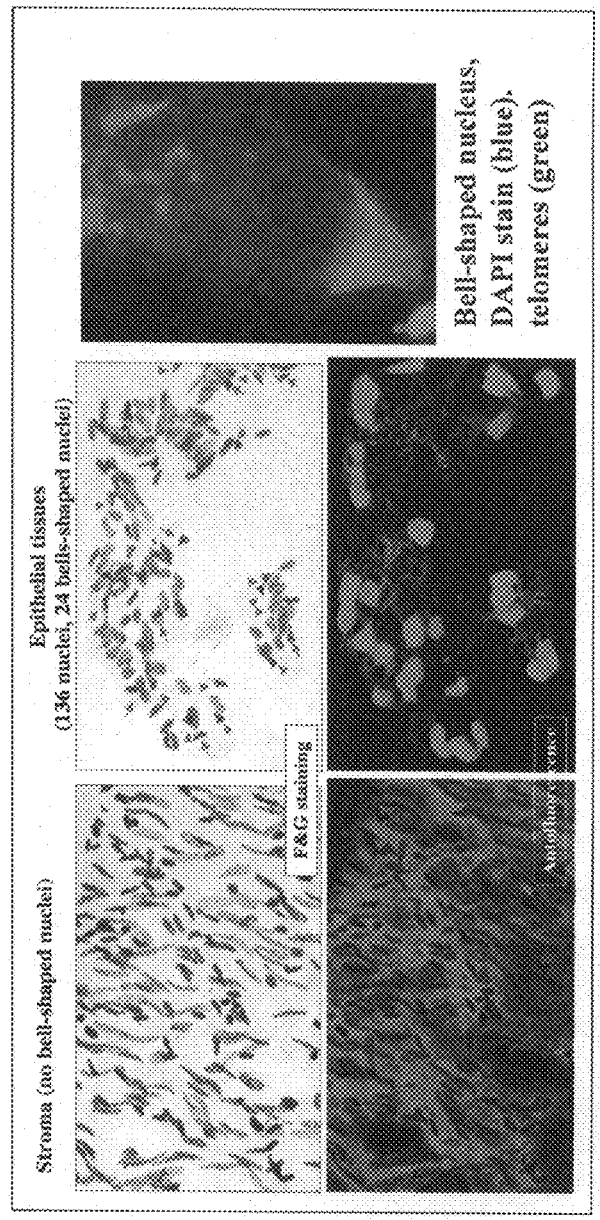
FIG. 20 shows that in human fetal epithelia every bell-shaped nucleus is associated with a brightly fluorescent balloon-shaped cytoplasmic structure that does not contain DNA. Human fetal colon tissue at 12 weeks is shown. Syncytia disappear at ~12 weeks of fetal life (the end of organogenesis). Bell-shaped nuclei are distributed throughout growing tissues.
Figure 22:
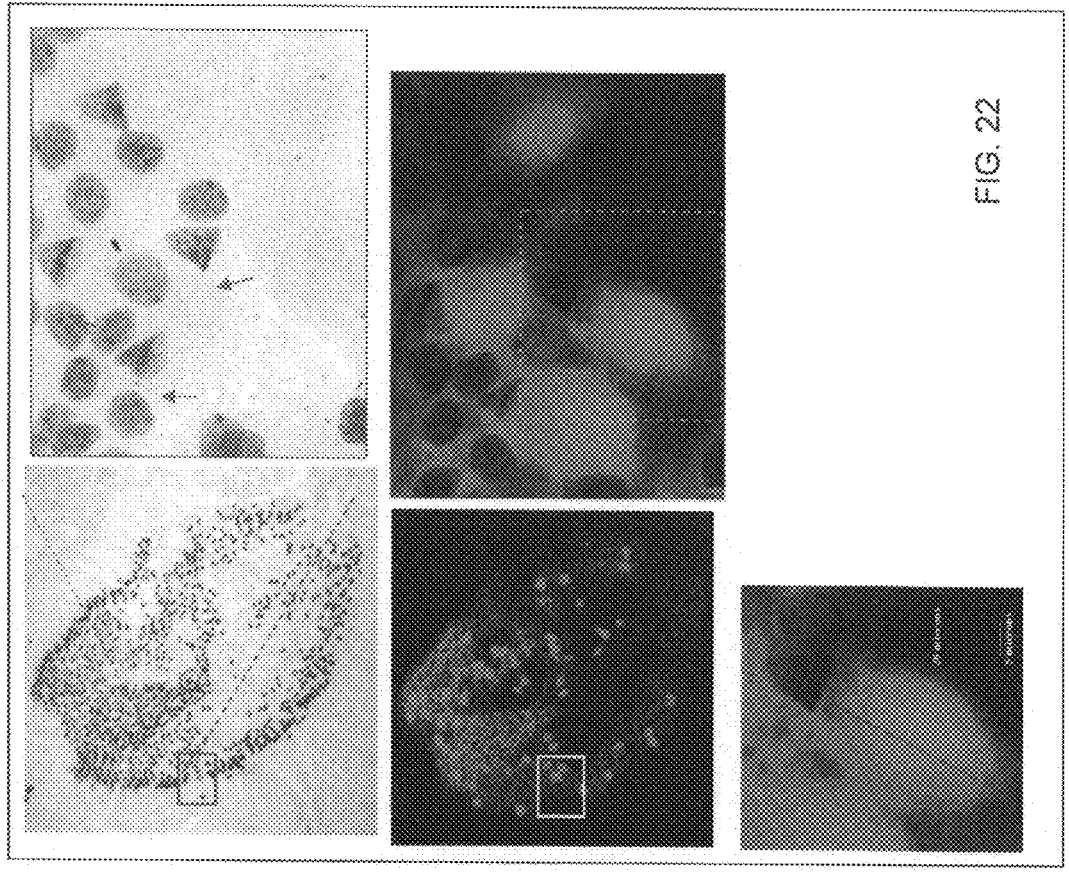
FIG. 22 shows the distribution of bell-shaped nuclei and fluorescent "balloons" in the villi of the small intestine of a human 14-16 week fetal discard. These brightly fluorescent balloon structures, physically associated with bell-shaped nuclei, are found throughout human fetal epithelia and derived adenocarcinomas of all tissues examined (see Example 5).
Figure 21:
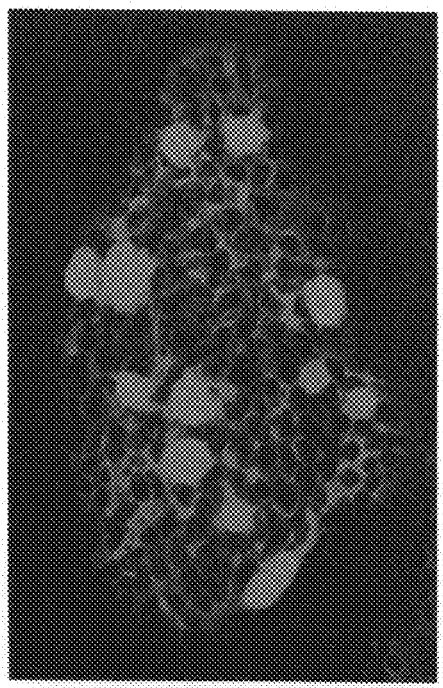
FIG. 21 shows that fetal epithelial tissue later organizes itself with these cellular forms easily recognizable by fluorescence alone. Acetic acid:ethanol fixative and Feulgen reagents were applied in this and other examples. Shown is human fetal small intestinal villus (9 wks) demonstrating Feulgen (green) fluorescence as described herein.
Figure 23:
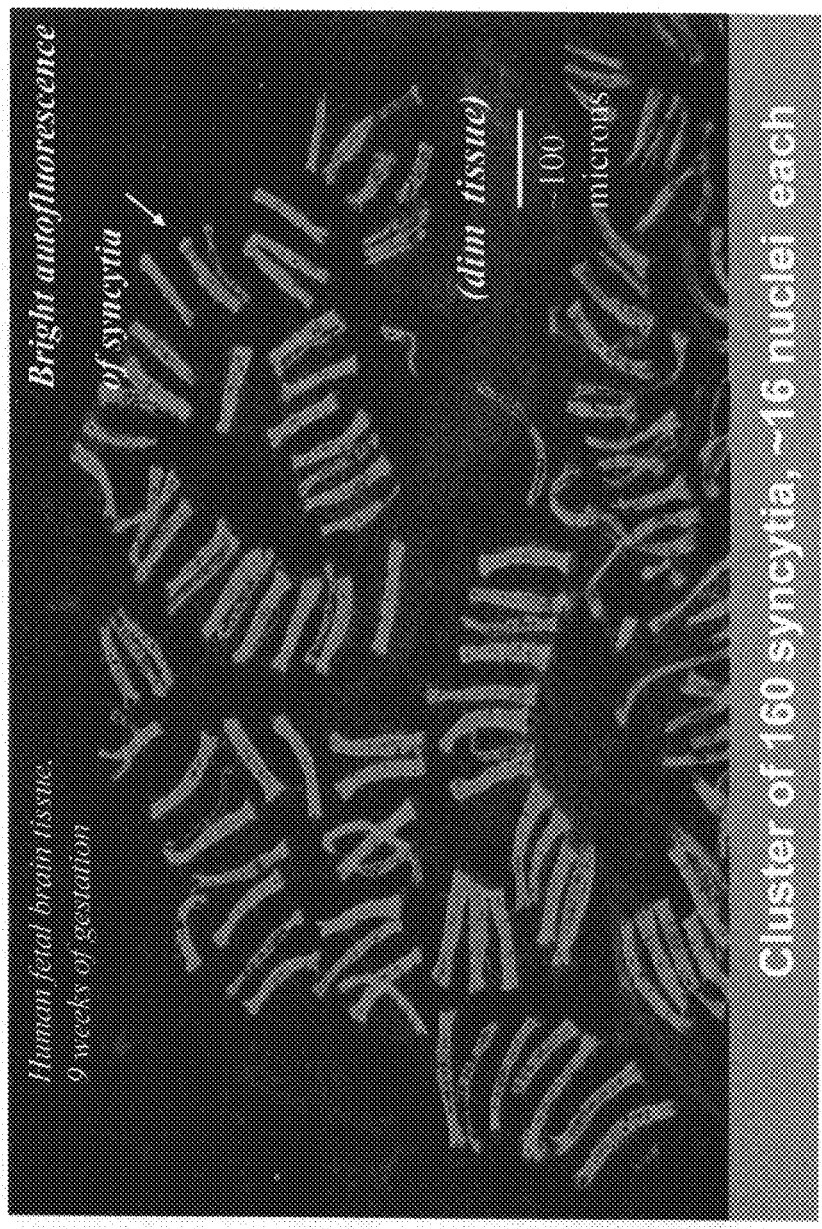
FIG. 23 shows an image of brightly fluorescent syncytia each containing bell-shaped nuclei from human fetal brain at nine weeks of gestation. Note syncytia are arranged in aggregates of multiple syncytia and multiple aggregates are non-randomly distributed in brain as in other developing tissues derived from endoderm, mesoderm or ectoderm. No fluorescent material has been added to these preparations that were simply fixed in acetic acid:ethanol upon surgical removal and subsequently treated with Feulgen reagent.
Figure 24:
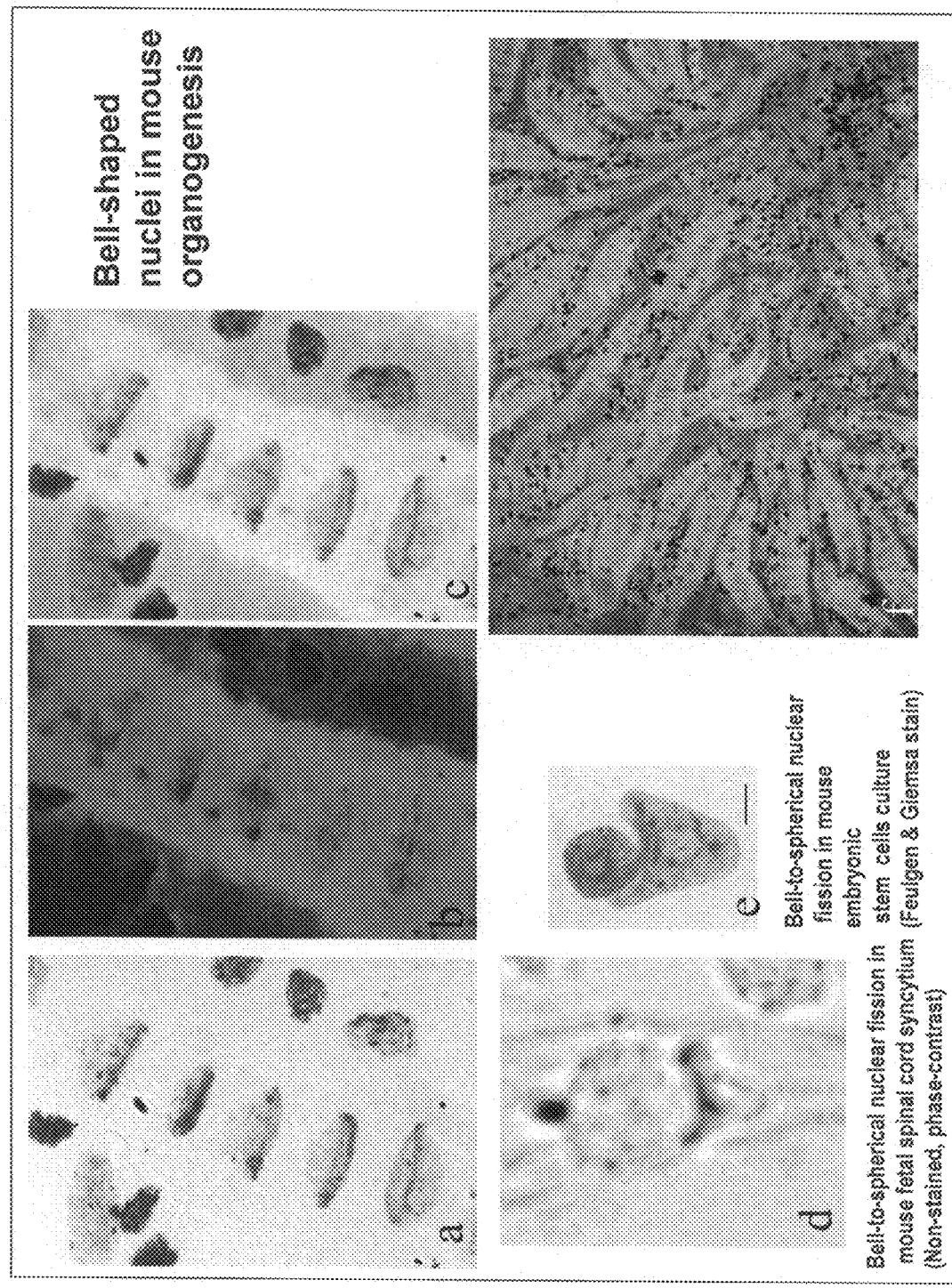
FIG. 24A (upper left) shows an image in bright field (not fluorescent) of fetal mouse intestine showing individual bell shaped nuclei in which Feulgen stain colors DNA purple and identifies bell-shaped structures as nuclei.
FIG. 24B (upper middle) shows same field as in FIG. 24A (upper left) but now showing bright fluorescence engulfing each bell-shaped nucleus. No fluorescent material has been added to these preparations that were simply fixed in acetic acid:ethanol upon surgical removal and subsequently treated with Feulgen reagent.
FIG. 24C (upper right) shows same field as in FIGS. 24A/24B (upper left, upper middle) but now showing superimposition of images demonstrating that bell-shaped nuclei are ensheathed in syncytium. No fluorescent material has been added to these preparations that were simply fixed in acetic acid:ethanol upon surgical removal and subsequently treated with Feulgen reagent.
FIG. 24D (lower left) shows phase contrast image of a bell-shaped nucleus giving rise to a spherical nucleus by amitotic asymmetrical nuclear fission in fetal mouse brain.
FIG. 24E (lower middle) shows image of a bell-shaped nucleus giving rise to a spherical nucleus by amitotic asymmetrical nuclear fission in cultured cell strain derived from fetal mouse muscle. Feulgen stain colors DNA purple and identifies bell-shaped structures as nuclei when observed with standard microscopy with transmitted light, i.e. not using fluorescence microscopy.
FIG. 24F (lower right) shows aggregate of fluorescent syncytia in which bell-shaped nuclei are stained purple by Feulgen reagent in developing fetal mouse organ.
Figure 25:
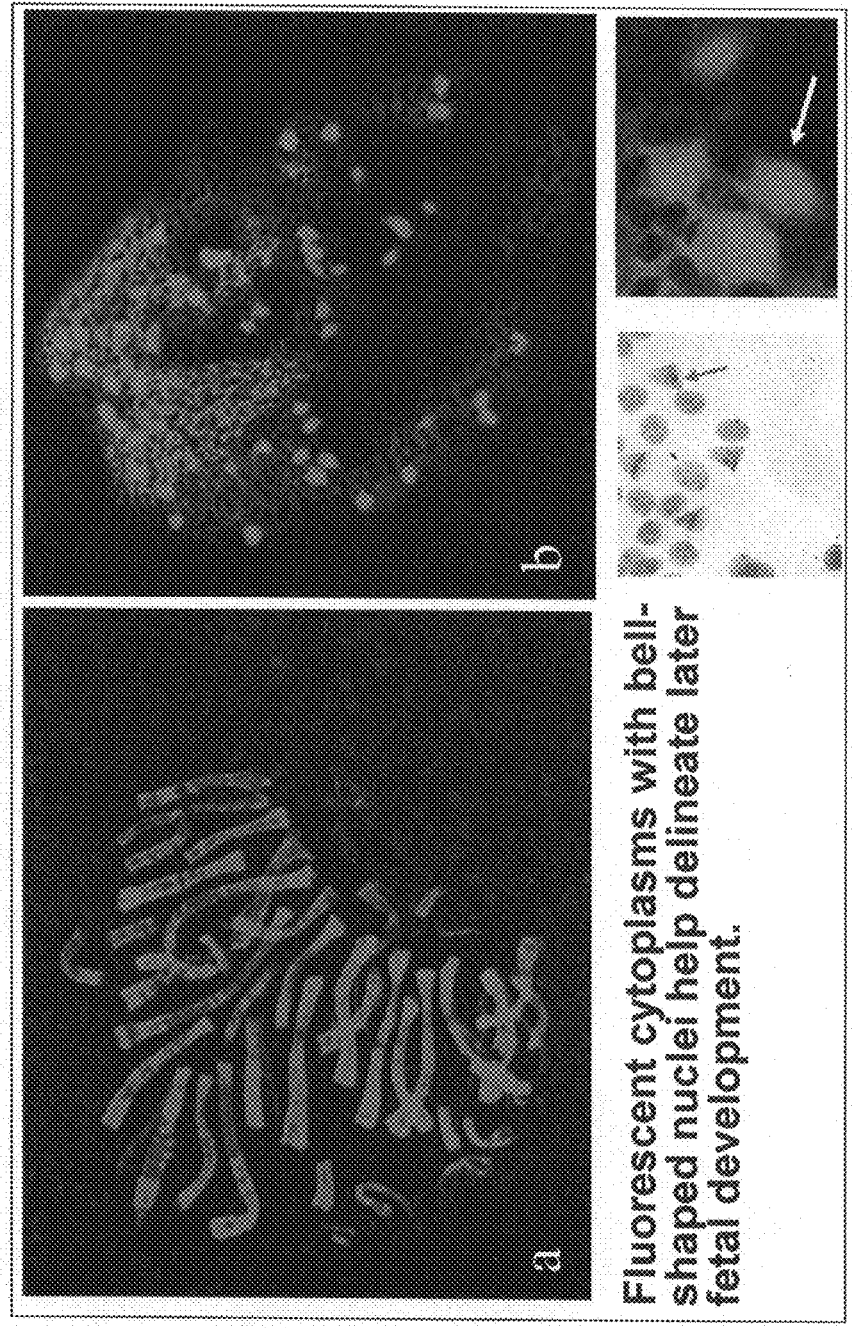
FIG. 25A (upper left) shows brightly fluorescent syncytia each containing multiple bell-shaped nuclei forming an aggregate of syncytia in the small intestine of a human 12 week fetus. No fluorescent material has been added to these preparations that were simply fixed in acetic acid:ethanol upon surgical removal and subsequently treated with Feulgen reagent.
FIG. 25B (upper right) shows brightly fluorescent balloon-like structures visible at low magnification in the small intestine of a human 14 week fetus. No fluorescent material has been added to these preparations that were simply fixed in acetic acid:ethanol upon surgical removal and subsequently treated with Feulgen reagent. Intensity and clarity of individual fluorescent structures' images is sufficient to permit automated scanning of tissue and tumor preparations for the presence of stem cells and to enumerate them.
Figure 26:
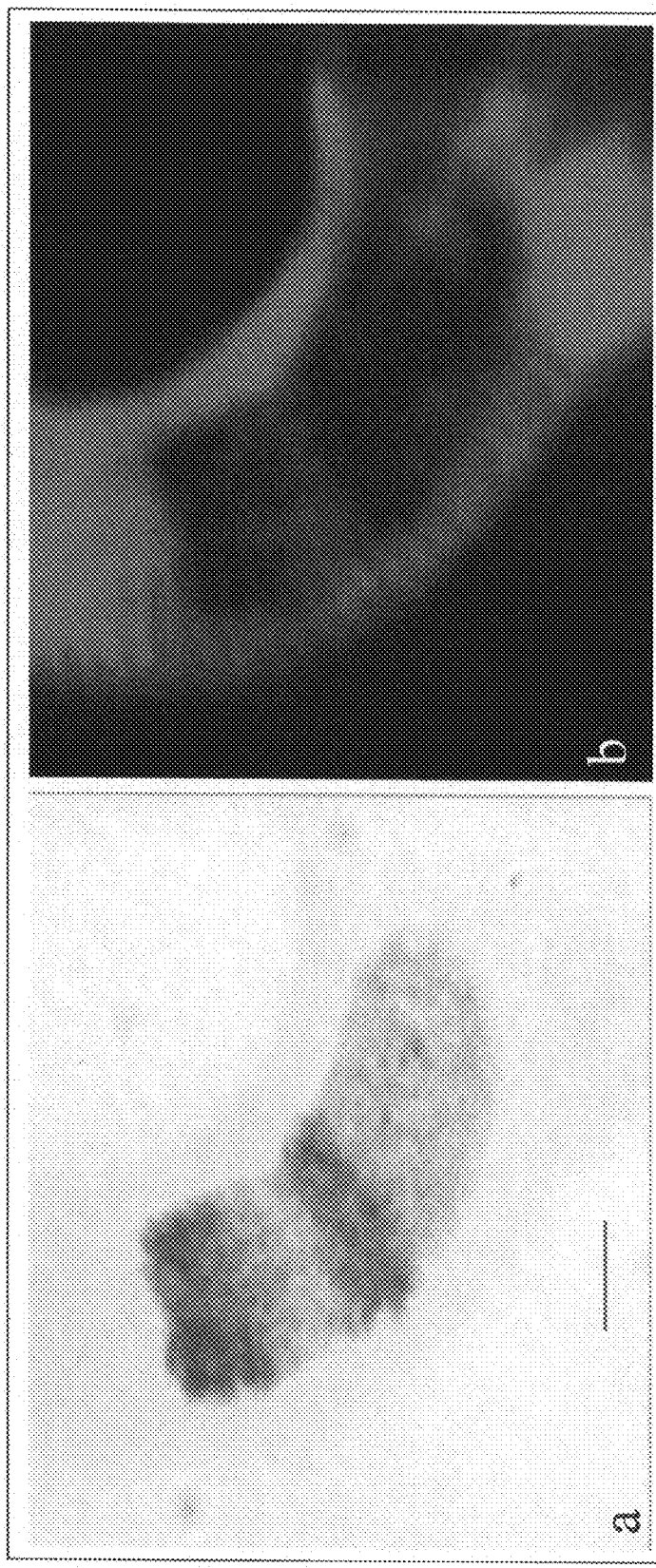
FIG. 26A (left) shows higher magnification mage in bright field (not fluorescent) showing individual bell-shaped nuclei of fetal tissue within a multinuclear syncytium undergoing symmetrical nuclear fission in which Feulgen stain colors DNA purple and identifies bell-shaped structures as nuclei.
FIG. 26B (right) shows same field as in FIG. 26A (left) but now showing brightly fluorescent material engulfing each bell-shaped nucleus. Note striations in syncytial wall at exact separation distance of sarcomeric arrangement of actin myosin that identifies syncytial walls as comprising contractile elements. Intensity and clarity of fluorescent images of syncytia are sufficient for automated slide scanning to detect said syncytia. No fluorescent material has been added to these preparations that were simply fixed in acetic acid:ethanol upon surgical removal and subsequently treated with Feulgen reagent.
Figure 27:
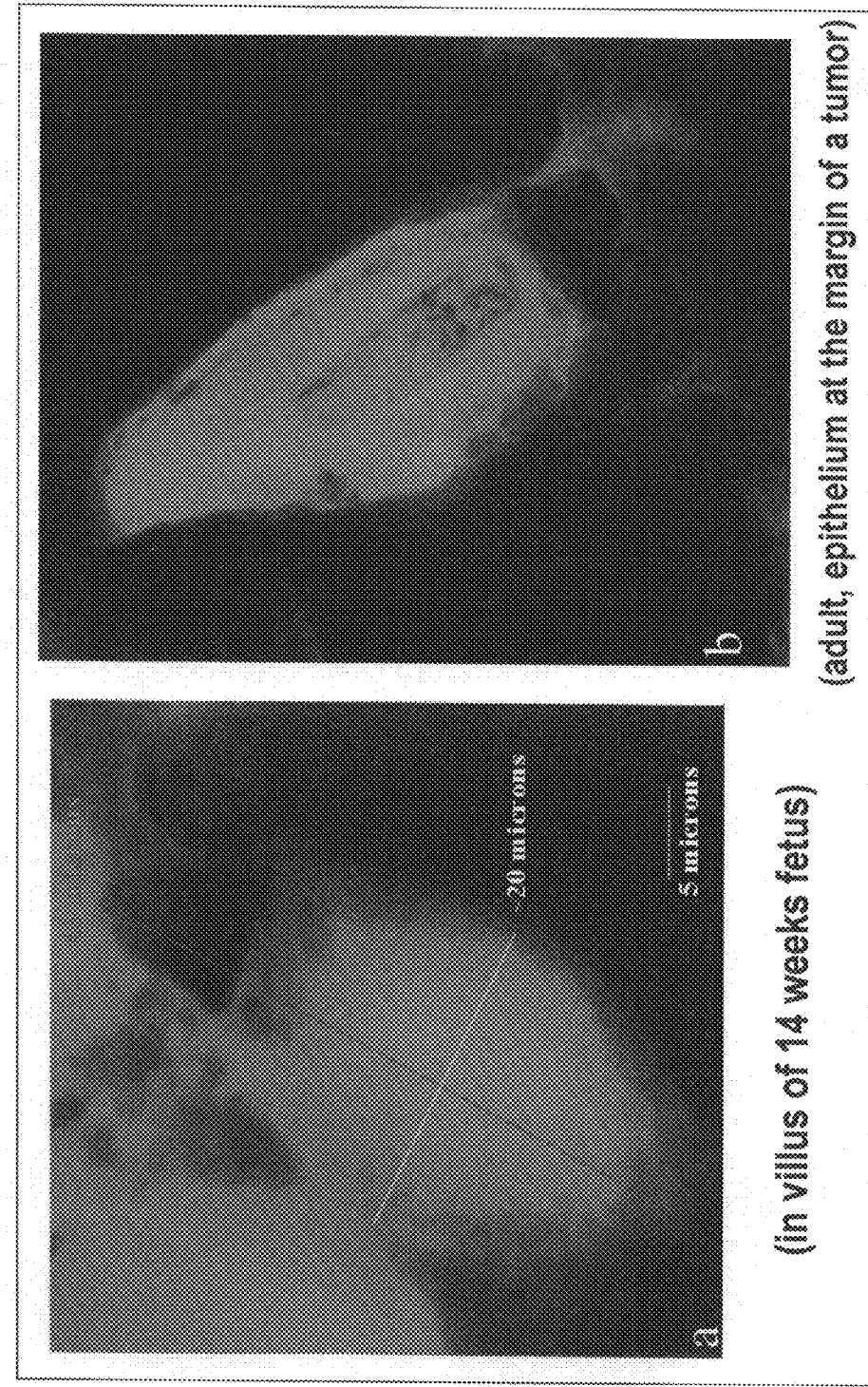
FIG. 27A (left) shows high resolution image demonstrating intense fluorescence (green) of balloon-like structure intimately associated with a bell-shaped nucleus in the developing small intestine of a 14 week human fetus.
FIG. 27B (right) shows high resolution image demonstrating intense fluorescence (green) of balloon-like structure intimately associated with a bell-shaped nucleus undergoing amitotic asymmetrical nuclear fission in the developing small intestine of a 14 week human fetus. Note that the derived "bullet-shaped" nucleus is at this stage enclosed in the fluorescent balloon-like structure.

An array of distinct closed nuclear forms has been found in fetal hindgut, colonic adenomas and adenocarcinomas that appear to arise ab initio from asymmetrical nuclear fission from bell-shaped nuclei but subsequently divide by mitosis and die by apoptosis. The shared set of nuclear forms in fetuses and tumors that are absent in adult tissue support the 19th century hypothesis that tumors were "embryonic" growths in adult organs (FIG. 9). These findings coupled with computer based image analysis and laser assisted micro dissection make the recognition and collection of large numbers of cells with specific nuclear morphologies possible. The characterization of the arrays of molecular and biochemical constituents in cells with bell-shaped nuclei as well as cells of other nuclear morphotypes peculiar to tumors should provide a previously unexpected set of potential therapeutic targets.

Oncogenesis like ontogenesis appears to proceed by lineal descent through an expanding set of stem cells. Only a small fraction of cells from a human tumor have the capacity to form new tumors as xenografts in immuno-suppressed rodents. Limiting dilution xenograft experiments were interpreted to indicate that the putative tumorigenic cells displayed stem cell like properties in that they were capable of generating new tumors containing additional stem cells as well as regenerating the phenotypically mixed populations of cells present in the original tumor (Singh, S. et al., 2004. *Oncogene*, 23:7267-7273; Clarke, M., 2005. *Biol. Blood Marrow Transplant.*, 11:14-26). However, more recently xenografted tumors have been found to be deficient in the highly differentiated tissue forms of human adenocarcinomas in vivo and in particular grow much faster than human tumors and xenografted tumors are remarkable for the absence of bell-shaped nuclei. It is postulated that tumor stem cells that form xenografts represent a truly embryonic form of cancer stem cell that rarely appears in human experience.

Modern restatement of the hypothesis that tumors are in fact reasonably well organized heterogeneous fetal structures has been reviewed and extended (Sell, S., 2004. *Crit. Rev.*

*Oncol. Hematol.*, 51:1-28). "Carcinofetal" stem cells would be expected to increase in number and give rise to differentiated cell types populating the highly heterogeneous niches within the tumor mass.

Various antigenic markers employed throughout the stem cell field have been used to enrich for cells capable of regenerating tissues or tumors often to a high degree, but no cells within these enriched populations have demonstrated any microscopic morphological cellular property that marks them as stem cells. If it is true that tumors arise from a single stem cell, a means is required to identify them and to collect them as homogeneous population of stem cells sufficient for analysis of molecular and biochemical analytes.

One method to achieve this goal relies on laser capture microdissection (LCM) to select and collect the tens of thousands of cells necessary for macromolecular array analyses and homogeneous with regard to microhistological properties that identify tumor stem cells. Alternately, dispersed cells with stem cell associated surface markers of tumors have been enriched by flow cytometry and cell sorting from heterogeneous cell populations (Morrison, S. et al., 1999. *Cell*, 96:737-749; Suzuki, A. et al., 2004. *Diabetes*, 53:2143-2152).

Another method would not involve the use of markers or fluorescent labels. As bell-shaped nuclei are associated with fluorescent balloon-like cytoplasmic structures in the absence of extraneous or exogenously added fluorescent dyes, methods for separating and sorting cells based on detecting and isolating these fluorescent structures is encompassed by the methods herein. Excitation with, for example, light produced with a halogen bulb, causes the balloon-like structures to emit green light—a property that can be exploited in identifying tumor pathology or for identifying and isolating stem cells.

The primary targets of existing methods of cancer therapeutics are cells transiting the cell cycle (Gomez Vidal, J. et al., 2004. *Curr. Top. Med. Chem.*, 4:175-202; Fischer, P. and Gianella Borradori, A., 2005. *Expert Opin. Investig. Drugs*, 14:457-477). No distinction is made between cells in transit between adult maintenance stem cells that divide to provide transition cells to replace the loss of terminal cells lost by programmed cell death and tumor stem cells. Therapy aims at the narrow window of regimens that kill all tumor stem cells without killing the patient, but adult maintenance stem cells would logically be expected to have the property of zero net cell growth while tumor stem cells, like fetal stem cells, are by definition involved in rapid net cell growth. Adult maintenance stem cell divisions would seem per force to be asymmetrical in nature giving rise to a new maintenance stem cell and a first differentiated transition cell. Tumor stem cells would require successive symmetrical nuclear divisions to support net tumor growth. It is in the discovery of bell-shaped nuclei undergoing symmetrical "cup from cup" nuclear division in tumors that a specific target for cytostatic or cytocidal therapies has been identified.

One theory lending support to this is the theory that tumors could by asphyxiated by preventing angiogenesis (Folkman, J. and Ingber, D., 1992. *Sem. Cancer Biol.*, 3:88-96). Creating hypoxia may recreate the conditions of early embryogenesis so far as tumor stem cells are concerned and may explain the palliative but not curative effects of anti angiogenic tactics. Blocking differentiation in tumors may block differentiation in normal tissues with undesirable consequences. Understanding that current cancer therapies are only minimally effective because the stem cells can repopulate tumors in a short period of time has become a powerful stimulus to the search for molecular and biochemical characteristics peculiar to tumor stem cells as opposed to adult maintenance stem cells. Such molecular and/or biochemical characteristics of tumor stem cells serve as targets in cancer therapeutics.

A key aspect of testing such theories and characterizing (molecular and biochemical properties) neoplastic stem cells and other neoplastic cell types is their isolation in sufficient numbers and degree of purity to permit quantitative chemical and biochemical analyses. Several means can be employed to obtain such cellular isolates. Laser capture microdissection, for example, is a method known in the art that allows one of skill in the art to manually select and microdissect batches of 10,000 bell-shaped nuclei from undifferentiated niches of colonic and pancreatic tumors. Cells 'catapulted' into the receiving vial are spread on microscope slides and scored as "bell", "not bell" or "indeterminate" on the basis of morphology. When a reasonable level of enrichment is reached (>75% of isolated nuclei scored as "bell"), the procedure is varied to preserve mRNA, proteins etc. for further analyses.

Existing protocols to isolate live colonic epithelium cells isolation have been adapted for continued observations in cell culture that preserve their structural and functional characteristics (Stich, M. et al., 2003. *Pathol. Res. Pract.*, 199:405 409; Micke, P. et al., 2004. *J. Pathol.*, 202:130 138). Isolated cells or syncytia with bell-shaped nuclei can be placed in slowly stirred microcarrier flasks with varying oxygen concentrations to mimic the oxygen levels expected in early embryos and unvascularized tumor niches. Medium replete with glutamine but lower in glucose than "standard" cell culture media formulations is also used to encourage growth of cells and syncytia with these bell-shaped nuclei so they can be studied under controlled laboratory conditions. Application of these methodologies is reasonably expected to yield a homogeneous cellular preparation with regard to nuclear morphology, mode of division and/or presence in special forms of multicellular aggregates or syncytia. These cells can also be isolated in a manner such that they can be propagated and studied in cell or tissue culture.

EXAMPLE 5

Balloon-like Structures Associated with Bell-Shaped Nuclei

Cellular bell-shaped nuclei were observed to be physically associated with balloon-like cytoplasmic structures. These balloon-like cytoplasmic structures were observed in embryonic fetal and tumor tissue samples (see FIGS. 20-27).

The fluorescent properties of these balloon-like structure in the absence of extraneous or exogenously added fluorescent dyes allow for their detection in methods useful in characterizing tissues samples (e.g., neoplastic, pre-neoplastic) or the developmental stage of tissue samples (e.g., embryonic). Fluorescence is the property of some atoms and molecules to absorb light at a particular wavelength and to subsequently emit light of longer wavelength after a brief interval, termed the fluorescence lifetime. The observation that the balloon-like structures fluoresce (they do not require labeling with an exogenous fluorophore), allows for the rapid identification of cells with bell-shaped nuclei.

Where bell-shaped nuclei are indicative of a particular developmental stage, e.g., fetal tissue, the identification of balloon-like structures associated with bell-shaped nuclei, e.g., by detecting their fluorescence, is indicative of a particular developmental stage. Alternatively, in adult tissues, detection of balloon-like structures associated with bell-shaped nuclei is indicative of neoplasia or pre-neoplasia in a suspect lesion.

In addition, as cells with bell-shaped nuclei have been observed to divide asymmetrically, they are pluripotent. As pluripotency is a hallmark feature of stem cells, the detection of balloon-like structures associated with bell-shaped nuclei allows for a rapid screening of cells for the identification and isolation of stem cells. Methods for detecting and isolating cells with such balloon-like structures, e.g., methods for sorting and isolation based on the fluorescence of cells with these balloon-like structures, are known in the art. Cells isolated in such a way have enormous potential in, for example, regenerative tissue therapies.

EXAMPLE 6

In Vitro Culture of Metakaryocytes

Figure 28:
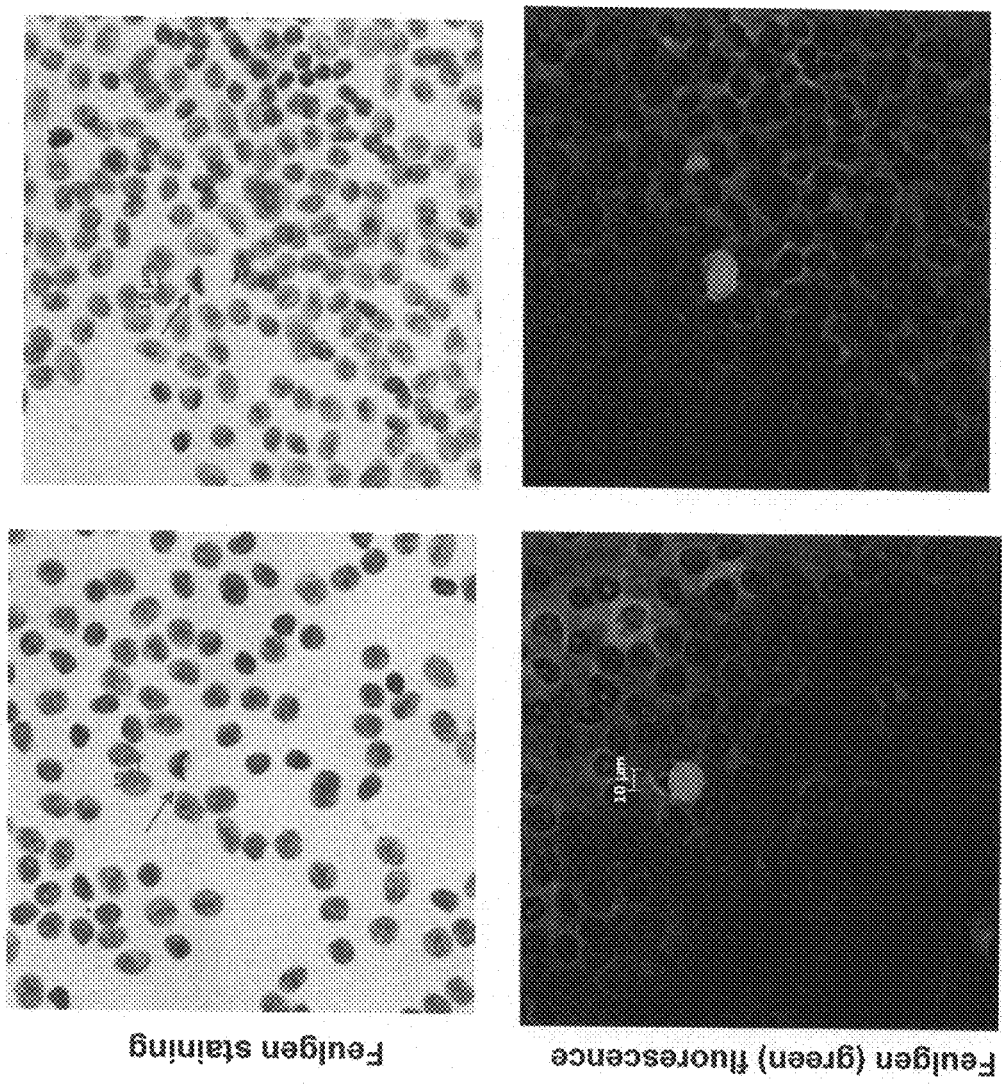
FIG. 28 are photographs of the HT29 human colon adenocarcinoma cell line cultured in vitro as described herein, and which have been fixed and stained with Feulgen stain, also as described herein. Shown are the microscopic images of cultured HT29 cells under standard transmitted light microscopy and the same field of cells observed using fluorescence microscopy. The fluorescent balloon-like structure of cells with a bell-shaped nucleus is found in approximately 1 to $10 \times 10^{-4}$ total HT29 cells.

The human cancer cell line, HT29, a human colon adenocarcinoma grade II cell line, was cultured in vitro, in MEM in the absence of glucose or sodium bicarbonate and in the presence of 5 mM fructose, 2.5% or 5% horse serum, and without $CO_2$ in the culture atmosphere. In vitro culture of HT29 cells under these conditions has a frequency of ~1 to $10\times10^{-4}$ metakaryotic cells [i.e., 1 to 10 cells in every 10,000 HT29 cells is a metakaryote) (see FIG. 28). Representative high resolution photographs of in vitro cultured HT29 cells fixed and stained with Feuglen's reagent as described herein, and in the absence of extraneous or exogenously added fluorescent reagents is provided in FIGS. 29 and 30.

The HT29 cell line grown under these conditions form small, button shaped colonies after individual cells are dispersed on a cell culture surface. Nearly all cells contain spherical or ovoid nuclei and can be seen to divide by mitotic nuclear fission. However, a distinct minority of some 1/1000 to 1/10,000 cells are observed to contain bell-shaped nuclei associated with balloon shaped cytoplasms rendered intensely fluorescent by the method described herein. Said cells with bell shaped nuclei have been observed to undergo live amitotic nuclear fission in phase contrast microscopy and many examples of both symmetrical and asymmetrical amitotic nuclear fissions have been observed in fixed HT29 cell culture specimens.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for identifying a metakaryotic stem cell of interest having a bell-shaped nucleus, the method comprising:
   a) fixing a sample of cells with an acid-alcohol mixture;
   b) treating said sample with a Feulgen's reagent with fuchsin as the Schiff's base;
   c) maintaining said sample in contact with the Feulgen's reagent in order to stain the sample in the absence of extraneous or exogenously added fluorescent dyes;
   d) exposing said stained sample to an excitation light from a light source; and
   e) visualizing green-light emitting fluorescent balloon-like cytoplasmic structures of a metakaryotic stem cell by fluorescence microscopy, thereby identifying the metakaryotic stem cell of interest in the sample.

2. The method of claim 1 wherein fixing the sample comprises treating the sample of cells with Carnoy's fixative.

3. The method of claim 1 wherein the cell is obtained from, or contained in a cell culture, a pre-neoplastic lesion, a tumor sample or a tissue sample.

4. The method of claim 3, wherein the metakaryotic stem cell is isolated from the tissue sample, pre-neoplastic lesion, or tumor sample.

5. The method of claim 1, wherein the metakaryotic stem cell comprises one or more amitotic, asymmetric nuclear division complexes.

6. The method of claim 1, wherein the metakaryotic stem cell is selected from the group consisting of an organ-specific stem cell, a cancer stem cell, a fetal-juvenile stem cell and an adult stem cell.

7. A method for diagnosing preneoplasia or neoplasia in an adult mammal suspected of having preneoplasia or neoplasia, the method comprising:
   a) fixing a sample of cells obtained from the adult mammal with an acid-alcohol mixture;
   b) treating said sample with a Feulgen's reagent with fuchsin as the Schiff's base;
   c) maintaining said sample in contact with the Feulgen's reagent in order to stain the sample in the absence of extraneous or exogenously added fluorescent dyes;
   d) exposing said stained sample to an excitation light from a light source; and
   e) detecting green-light emitting fluorescent balloon-like cytoplasmic structures of a metakaryotic stem cell in the sample by fluorescence microscopy, whereby detecting the presence of one or more green-light emitting fluorescent metakaryotic stem cells having a bell-shaped nucleus in the absence of extraneous or exogenously added fluorescent dyes is indicative of preneoplasia or neoplasia in the adult mammal.

8. The method of claim 7 wherein fixing the sample comprises treating the sample of cells with Carnoy's fixative.

9. The method of claim 7, wherein the metakaryotic stem cell comprises one or more amitotic, asymmetric nuclear division complexes.

* * * * *